(12) United States Patent
Bédard et al.

(10) Patent No.: US 9,526,636 B2
(45) Date of Patent: *Dec. 27, 2016

(54) INSTRUMENTED PROSTHETIC FOOT

(75) Inventors: Stéphane Bédard, Québec (CA); Pierre-Olivier Roy, Sainte-Foy (CA)

(73) Assignee: Victhom Laboratory Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/869,559

(22) Filed: Aug. 26, 2010

(65) Prior Publication Data

US 2011/0130847 A1    Jun. 2, 2011

Related U.S. Application Data

(63) Continuation of application No. 12/260,479, filed on Oct. 29, 2008, now Pat. No. 7,815,689, which is a
(Continued)

(51) Int. Cl.
*A61F 2/66* (2006.01)
*A61F 2/60* (2006.01)
(Continued)

(52) U.S. Cl.
CPC . *A61F 2/66* (2013.01); *A61F 2/60* (2013.01); *A61F 2/68* (2013.01); *A61F 2/72* (2013.01); *A61F 2002/5001* (2013.01); *A61F 2002/5003* (2013.01); *A61F 2002/5007* (2013.01); *A61F 2002/665* (2013.01); *A61F 2002/6621* (2013.01); *A61F 2002/6642* (2013.01);
(Continued)

(58) Field of Classification Search
CPC ............ A61F 2/66; A61F 2/68; A61F 2/6607;
A61F 2002/5003; A61F 2002/7635; A61F 2002/701; A61F 2002/6614; A61F 2002/7625; A61F 2002/764; A61F 2002/7645; A61F 2/60
USPC .............................................. 623/24, 46–57
See application file for complete search history.

(56) References Cited

U.S. PATENT DOCUMENTS 2,568,051 A    9/1951  Catranis
2,619,652 A    12/1952 Vesper
(Continued)

FOREIGN PATENT DOCUMENTS

CA        2405356        10/2001
CA        2494365        3/2004
(Continued)

OTHER PUBLICATIONS

Australian Office Action dated Apr. 29, 2008 in Application No. 2003286025, filed Nov. 18, 2003.
(Continued)

*Primary Examiner* — Howie Matthews
(74) *Attorney, Agent, or Firm* — Knobbe, Martens, Olson & Bear, LLP

(57) ABSTRACT

The present invention discloses an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

9 Claims, 15 Drawing Sheets

Related U.S. Application Data continuation-in-part of application No. 10/715,989, filed on Nov. 18, 2003, now abandoned.

(51) Int. Cl.
  *A61F 2/68* (2006.01)
  *A61F 2/72* (2006.01)
  *A61F 2/50* (2006.01)
  *A61F 2/70* (2006.01)
  *A61F 2/76* (2006.01)

(52) U.S. Cl.
  CPC . *A61F 2002/6685* (2013.01); *A61F 2002/705* (2013.01); *A61F 2002/764* (2013.01); *A61F 2002/7635* (2013.01); *A61F 2002/7685* (2013.01)

(56) References Cited

U.S. PATENT DOCUMENTS

| | | |
|---|---|---|
| 2,843,853 A | 7/1958 | Mauch |
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,589,134 A | 6/1971 | Hackmann |
| 3,659,294 A | 5/1972 | Glabiszewski |
| 3,701,368 A | 10/1972 | Stern |
| 3,791,375 A | 2/1974 | Pfeiffer |
| 3,820,168 A | 6/1974 | Horvath |
| 3,866,246 A | 2/1975 | Seamone et al. |
| 3,871,032 A | 3/1975 | Karas |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie |
| 4,354,676 A | 10/1982 | Ariel |
| 4,370,977 A | 2/1983 | Mauldin et al. |
| 4,386,891 A | 6/1983 | Riefel et al. |
| 4,387,472 A | 6/1983 | Wilson |
| 4,433,679 A | 2/1984 | Mauldin et al. |
| 4,441,644 A | 4/1984 | Farian |
| 4,458,367 A | 7/1984 | May |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Roung et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,012,591 A | 5/1991 | Asakawa |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Barringer et al. |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe et al. |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnäs |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman |
| 5,376,133 A | 12/1994 | Gramnas |
| 5,376,137 A | 12/1994 | Shorter et al. |
| 5,376,138 A | 12/1994 | Bouchard et al. |
| 5,382,373 A | 1/1995 | Carlson et al. |
| 5,383,939 A | 1/1995 | James |
| 5,394,132 A | 2/1995 | Poil |
| 5,397,287 A | 3/1995 | Lindfors |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts et al. |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,472,412 A | 12/1995 | Knoth |
| 5,476,441 A | 12/1995 | Durfee et al. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |

(56) References Cited

U.S. PATENT DOCUMENTS

| | | |
|---|---|---|
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriquez |
| 5,800,568 A | 9/1998 | Atkinson et al. |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,947,238 A | 9/1999 | JollR et al. |
| 5,948,021 A | 9/1999 | Radcliffe |
| 5,955,667 A | 9/1999 | Fyfe |
| 5,957,981 A | 9/1999 | Gramnas |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,998,930 A | 12/1999 | Upadhyay et al. |
| 6,006,412 A | 12/1999 | Bergmann et al. |
| 6,007,582 A | 12/1999 | May |
| RE36,521 E | 1/2000 | Hiemisch |
| 6,039,091 A | 3/2000 | Rodgers et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,690 A | 10/2000 | Hamlin et al. |
| 6,129,766 A | 10/2000 | Johnson et al. |
| 6,139,586 A | 10/2000 | Wagner et al. |
| 6,151,624 A | 11/2000 | Teare et al. |
| 6,164,967 A | 12/2000 | Sale |
| 6,165,226 A | 12/2000 | Wagner |
| 6,168,634 B1 | 1/2001 | Schmitz |
| 6,183,425 B1 | 2/2001 | Whalen et al. |
| 6,185,614 B1 | 2/2001 | Cuomo et al. |
| 6,187,051 B1 | 2/2001 | van de Veen |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,206,934 B1 | 3/2001 | Phillips |
| 6,241,775 B1 | 6/2001 | Blatchford |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,395,193 B1 | 5/2002 | Kintz et al. |
| 6,409,695 B1 | 6/2002 | ConnellR |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,537,322 B1 | 3/2003 | Johnson et al. |
| 6,574,655 B1 | 6/2003 | Libert et al. |
| 6,589,287 B2 | 7/2003 | Lundborg |
| 6,599,439 B2 | 7/2003 | IRegar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,645,252 B2 | 11/2003 | Asai et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,719,806 B1 | 4/2004 | Zahedi et al. |
| 6,733,180 B2 | 5/2004 | Nakamura |
| 6,740,123 B2 | 5/2004 | Davalli et al. |
| 6,740,125 B2 | 5/2004 | Mosler |
| 6,743,260 B2 | 6/2004 | Townsend et al. |
| 6,755,870 B1 * | 6/2004 | Biedermann et al. .......... 623/24 |
| 6,761,743 B1 | 7/2004 | Johnson |
| 6,764,520 B2 | 7/2004 | Deffenbaugh et al. |
| 6,770,045 B2 | 8/2004 | Naft et al. |
| 6,780,343 B2 | 8/2004 | Hata |
| 6,805,677 B2 | 10/2004 | Simmons |
| 6,811,571 B1 | 11/2004 | Phillips |
| 6,813,582 B2 | 11/2004 | Levi et al. |
| D499,487 S | 12/2004 | Bedard et al. |
| D501,925 S | 2/2005 | Bedard et al. |
| 6,855,170 B2 | 2/2005 | Gramnas |
| 6,876,135 B2 | 4/2005 | Pelrine et al. |
| 6,908,488 B2 | 6/2005 | Passivaara |
| 6,910,331 B2 | 6/2005 | Asai et al. |
| 6,918,308 B2 | 7/2005 | Biedermann |
| 6,966,882 B2 | 11/2005 | Horst |
| 6,966,933 B2 | 11/2005 | Christensen |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,066,896 B1 | 6/2006 | Kiselik |
| 7,101,487 B2 | 9/2006 | Hsu et al. |
| 7,118,601 B2 | 10/2006 | Yasui et al. |
| 7,131,998 B2 | 11/2006 | Pasolini |
| 7,137,998 B2 | 11/2006 | Bedard |
| 7,147,667 B2 | 12/2006 | Bedard |
| 7,150,762 B2 | 12/2006 | Caspers |

(56) References Cited

U.S. PATENT DOCUMENTS

| | | |
|---|---|---|
| 7,164,967 B2 | 1/2007 | Etienne-Cummings et al. |
| 7,198,071 B2 | 4/2007 | Bisbee, III et al. |
| 7,209,788 B2 | 4/2007 | Nicolelis et al. |
| 7,279,009 B2 | 10/2007 | Herr et al. |
| 7,295,892 B2 | 11/2007 | Herr et al. |
| 7,308,333 B2 | 12/2007 | Kern et al. |
| 7,313,463 B2 | 12/2007 | Herr et al. |
| 7,314,490 B2 | 1/2008 | Bédard et al. |
| 7,381,192 B2 | 6/2008 | Brodard |
| 7,393,364 B2 | 7/2008 | Martin |
| 7,396,337 B2 | 7/2008 | McBean et al. |
| 7,410,338 B2 | 8/2008 | Schiele et al. |
| 7,410,471 B1 | 8/2008 | Campbell et al. |
| 7,410,472 B2 | 8/2008 | Yakimovich et al. |
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,485,152 B2 | 2/2009 | Haynes et al. |
| 7,503,900 B2 | 3/2009 | Goswami |
| 7,520,904 B2 | 4/2009 | Christensen |
| 7,531,006 B2 | 5/2009 | Clausen et al. |
| 7,575,602 B2 | 8/2009 | Amirouche et al. |
| 7,578,799 B2 | 8/2009 | Thorsteinsson et al. |
| 7,588,604 B2 | 9/2009 | Okuda |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bédard et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| 7,815,689 B2 | 10/2010 | Bedard et al. |
| 7,862,620 B2 | 1/2011 | Clausen et al. |
| 7,867,284 B2 | 1/2011 | Bedard |
| 7,867,285 B2 | 1/2011 | Clausen et al. |
| 7,883,546 B2 | 2/2011 | Kazerooni et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,955,398 B2 | 6/2011 | Bedard et al. |
| 7,985,265 B2 | 7/2011 | Moser et al. |
| 8,007,544 B2 | 8/2011 | Jonsson et al. |
| 8,048,172 B2 | 11/2011 | Jonsson et al. |
| 8,057,550 B2 | 11/2011 | Clausen et al. |
| 8,075,633 B2 | 12/2011 | Herr et al. |
| 8,083,807 B2 | 12/2011 | Auberger et al. |
| 8,087,498 B2 | 1/2012 | Dupuis et al. |
| 8,109,890 B2 | 2/2012 | Kamiar et al. |
| 8,122,772 B2 | 2/2012 | Clausen et al. |
| 8,142,370 B2 | 3/2012 | Weinberg et al. |
| 8,211,042 B2 | 7/2012 | Gilbert et al. |
| 8,231,687 B2 | 7/2012 | Bedard et al. |
| 8,287,477 B1 | 10/2012 | Herr et al. |
| 8,323,354 B2 | 12/2012 | Bedard et al. |
| 8,500,823 B2 | 8/2013 | Herr et al. |
| 8,512,415 B2 | 8/2013 | Herr et al. |
| 8,551,184 B1 | 10/2013 | Herr |
| 7,431,737 C1 | 12/2013 | Ragnarsdottir et al. |
| 8,617,254 B2 | 12/2013 | Bisbee, III et al. |
| 8,657,886 B2 | 2/2014 | Clausen et al. |
| 8,702,811 B2 | 4/2014 | Ragnarsdottir et al. |
| 7,896,927 C1 | 5/2014 | Clausen et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,986,397 B2 | 3/2015 | Bédard et al. |
| 9,044,346 B2 | 6/2015 | Langlois et al. |
| 9,066,819 B2 | 6/2015 | Gramnaes |
| 2002/0087216 A1 | 7/2002 | Atkinson et al. |
| 2002/0183803 A1 | 12/2002 | Fang et al. |
| 2002/0198604 A1 | 12/2002 | Schulman et al. |
| 2003/0019700 A1 | 1/2003 | Wittig |
| 2003/0120353 A1 | 6/2003 | Christensen |
| 2003/0149600 A1 | 8/2003 | Williams |
| 2004/0064195 A1 | 4/2004 | Herr |
| 2004/0083007 A1 | 4/2004 | Molino et al. |
| 2004/0111163 A1 | 6/2004 | Bedard et al. |
| 2004/0193286 A1 | 9/2004 | Grundei |
| 2004/0215111 A1 | 10/2004 | Bonutti et al. |
| 2005/0070834 A1 | 3/2005 | Herr et al. |
| 2005/0107889 A1 | 5/2005 | Bedard et al. |
| 2005/0137717 A1 | 6/2005 | Gramnas et al. |
| 2005/0216097 A1 | 9/2005 | Rifkin |
| 2005/0283257 A1 | 12/2005 | Bisbee et al. |
| 2006/0136072 A1 | 6/2006 | Bisbee et al. |
| 2006/0173552 A1 | 8/2006 | Roy |
| 2006/0184252 A1 | 8/2006 | Oddsson et al. |
| 2006/0184280 A1 | 8/2006 | Oddsson et al. |
| 2006/0189899 A1 | 8/2006 | Flaherty et al. |
| 2006/0249315 A1 | 11/2006 | Herr et al. |
| 2006/0259153 A1 | 11/2006 | Harn et al. |
| 2007/0016329 A1 | 1/2007 | Herr et al. |
| 2007/0027557 A1 | 2/2007 | Jonsson et al. |
| 2007/0043449 A1 | 2/2007 | Herr et al. |
| 2007/0050047 A1 | 3/2007 | Ragnarsdottlr et al. |
| 2007/0123997 A1 | 5/2007 | Herr et al. |
| 2007/0162152 A1 | 7/2007 | Herr et al. |
| 2008/0004718 A1 | 1/2008 | Mosler |
| 2008/0046096 A1 | 2/2008 | Bedard et al. |
| 2008/0306612 A1 | 12/2008 | Mosler |
| 2009/0030344 A1 | 1/2009 | Moser et al. |
| 2009/0265018 A1 | 10/2009 | Goldfarb et al. |
| 2009/0299480 A1 | 12/2009 | Gilbert et al. |
| 2009/0299489 A1 | 12/2009 | Gramnaes |
| 2010/0023133 A1 | 1/2010 | Fairbanks et al. |
| 2010/0113980 A1 | 5/2010 | Herr et al. |
| 2010/0131101 A1 | 5/2010 | Engeberg et al. |
| 2010/0161077 A1 | 6/2010 | Boone et al. |
| 2010/0179668 A1 | 7/2010 | Herr et al. |
| 2010/0185124 A1 | 7/2010 | Bisbee, III et al. |
| 2010/0185301 A1 | 7/2010 | Hansen et al. |
| 2010/0262260 A1 | 10/2010 | Bédard et al. |
| 2010/0305716 A1 | 12/2010 | Pusch et al. |
| 2010/0324456 A1 | 12/2010 | Jónsson et al. |
| 2010/0324699 A1 | 12/2010 | Herr et al. |
| 2011/0106274 A1 | 5/2011 | Ragnarsdottir et al. |
| 2011/0125290 A1 | 5/2011 | Langlois |
| 2011/0130847 A1 | 6/2011 | Bedard et al. |
| 2011/0137429 A1 | 6/2011 | Bedard |
| 2011/0224804 A1 | 9/2011 | Clausen et al. |
| 2011/0245931 A1 | 10/2011 | Clausen et al. |
| 2012/0016492 A1 | 1/2012 | Clausen |
| 2012/0191221 A1 | 7/2012 | Bedard et al. |
| 2012/0209405 A1 | 8/2012 | Herr et al. |
| 2012/0232672 A1 | 9/2012 | Ragnarsdottir et al. |
| 2013/0035769 A1 | 2/2013 | Bedard et al. |
| 2013/0144402 A1 | 6/2013 | Clausen et al. |
| 2013/0204395 A1 | 8/2013 | Gramnaes |
| 2013/0297041 A1 | 11/2013 | Bedard et al. |
| 2014/0081424 A1 | 3/2014 | Herr et al. |
| 2014/0156025 A1 | 6/2014 | Bisbee, III et al. |
| 2014/0277586 A1 | 9/2014 | Clausen |
| 2015/0032225 A1 | 1/2015 | Oddsson et al. |
| 2015/0073566 A1 | 3/2015 | Ragnarsdottir et al. |
| 2015/0164661 A1 | 6/2015 | Ragnarsdottir et al. |

FOREIGN PATENT DOCUMENTS

| | | |
|---|---|---|
| CA | 2543061 | 6/2005 |
| CH | 543277 | 12/1973 |
| CN | 2043873 | 9/1989 |
| CN | 1215614 | 5/1999 |
| CN | 2400072 Y | 10/2000 |
| DE | 3543291 | 6/1987 |
| DE | 3923056 | 1/1991 |
| DE | 3923057 | 1/1991 |
| DE | 4305213 | 8/1993 |
| DE | 4318901 | 1/1994 |
| DE | 42 29 330 | 3/1994 |
| DE | 19521464 A1 | 6/1995 |
| DE | 195 21 464 A | 3/1997 |

(56) References Cited

FOREIGN PATENT DOCUMENTS

| | | |
|---|---|---|
| EP | 0358056 | 3/1990 |
| EP | 0 380 060 | 8/1990 |
| EP | 0503775 | 9/1992 |
| EP | 0 549 855 | 7/1993 |
| EP | 0549855 | 7/1993 |
| EP | 0628296 | 12/1994 |
| EP | 0654254 A1 | 5/1995 |
| EP | 0718951 | 6/1996 |
| EP | 0902547 | 3/1999 |
| EP | 1066 793 | 1/2001 |
| EP | 1125825 | 1/2001 |
| EP | 1107420 | 6/2001 |
| EP | 1 166 726 | 1/2002 |
| EP | 1166726 | 1/2002 |
| EP | 1169982 A1 | 1/2002 |
| EP | 1 410 780 | 4/2004 |
| EP | 1417942 | 5/2004 |
| EP | 1 442 704 | 8/2004 |
| EP | 1 547 567 | 6/2005 |
| EP | 1 792 597 | 6/2007 |
| FR | 2293185 | 7/1976 |
| FR | 2623086 | 11/1987 |
| FR | 2 623 086 | 5/1989 |
| FR | 2816463 | 5/2002 |
| GB | 2 201 260 | 8/1988 |
| GB | 2 244 006 | 11/1991 |
| GB | 2 260 495 | 4/1993 |
| GB | 2 268 070 A | 1/1994 |
| GB | 2 301 776 | 12/1996 |
| GB | 2 302 949 | 2/1997 |
| GB | 2 334 891 | 9/1999 |
| GB | 2 338 653 | 12/1999 |
| GB | 2 343 848 | 5/2000 |
| GB | 2 367 753 | 4/2002 |
| JP | 59/32453 | 2/1984 |
| JP | 59/71747 | 4/1984 |
| JP | 59-088147 | 5/1984 |
| JP | S59189843 | 10/1984 |
| JP | 60081530 | 5/1985 |
| JP | 60-177102 | 9/1985 |
| JP | 01-244748 A | 9/1989 |
| JP | 03-181633 | 8/1991 |
| JP | 04-78337 | 3/1992 |
| JP | H05123348 | 5/1993 |
| JP | 5-161668 | 6/1993 |
| JP | H724766 | 1/1995 |
| JP | 11056885 | 3/1999 |
| JP | 11000345 | 6/1999 |
| JP | 11-215793 | 8/1999 |
| JP | 11-215793 A | 8/1999 |
| JP | 2001/277175 | 10/2001 |
| JP | 2001-277175 | 10/2001 |
| JP | 2002-191654 | 7/2002 |
| JP | 2002-219141 | 8/2002 |
| JP | 2003/250824 | 9/2003 |
| JP | 2005-500 A | 1/2005 |
| JP | 2009-153660 | 7/2009 |
| KR | 2002-0041137 | 6/2002 |
| SU | 1447366 A1 | 12/1988 |
| SU | 1731210 | 5/1992 |
| WO | WO 94/06374 | 3/1994 |
| WO | WO 94/09727 A2 | 5/1994 |
| WO | WO 95/26171 | 10/1995 |
| WO | WO 96/39110 | 12/1996 |
| WO | WO 96/41599 | 12/1996 |
| WO | WO 97/00661 | 1/1997 |
| WO | WO 97/27822 | 8/1997 |
| WO | WO 98/02552 A | 6/1998 |
| WO | WO 98/25552 | 6/1998 |
| WO | WO 98/25552 A | 6/1998 |
| WO | WO 98/38951 | 9/1998 |
| WO | WO 99/00075 | 1/1999 |
| WO | WO 99/05991 | 2/1999 |
| WO | WO 99/08621 | 2/1999 |
| WO | WO 99/29272 | 6/1999 |
| WO | WO 99/29272 A | 6/1999 |
| WO | WO 99/55261 | 11/1999 |
| WO | WO 00/27318 | 5/2000 |
| WO | WO 00/30572 | 6/2000 |
| WO | WO 00/38599 A1 | 7/2000 |
| WO | WO 00/71061 | 11/2000 |
| WO | WO 01/17466 | 3/2001 |
| WO | WO 01/72245 | 10/2001 |
| WO | WO 02/080825 | 10/2002 |
| WO | WO 03/003953 | 1/2003 |
| WO | WO 03/088373 | 10/2003 |
| WO | WO 2004/017871 A | 3/2004 |
| WO | WO 2004/017871 A2 | 3/2004 |
| WO | WO 2004/017890 | 3/2004 |
| WO | WO 2004/092606 | 10/2004 |
| WO | WO 2005/048887 | 6/2005 |
| WO | WO 2006/024876 | 3/2006 |
| WO | WO 2006/076164 | 7/2006 |
| WO | WO 2010/027968 A2 | 3/2010 |
| WO | WO 2011/100117 | 8/2011 |
| WO | WO 2011/100118 | 8/2011 |

OTHER PUBLICATIONS

Australian Office Action dated Jun. 23, 2009 in Application No. 2003286025, filed Nov. 18, 2003.
Canadian Office Action dated Jul. 5, 2010 in Application No. 2,543,061, filed Nov. 18, 2003.
Chinese Office Action dated Dec. 25, 2009 in Application No. 200380110708.2, filed Nov. 18, 2003.
Chinese Office Action dated Jan. 23, 2009 in Application No. 200380110708.2, filed Nov. 18, 2003.
Dietl, H., Der Einsatz von Elektronik bei Prothesen zur Versorgung der unteren Extremitat, Med. Orth. Tech 117 (1997)31-35.
Flowers et al., Journal of Biomedical Engineering: Transactions of the ASME; Feb. 1977, pp. 3-8.
Korean Office Action dated Jun. 11, 2010 in Application No. 10-2006-7009718, filed Nov. 18, 2003.
Abbas, J.J., et al., Neural Network Control of Functional Neuromuscular Stimulation Systems: Computer Simulation Studies, *IEEE Transactions on Biomedical Engineering* 42(11), Nov. 1995.
Andrews, B.J., et al., Hybrid FES Orthosis Incorporating Closed Loop Control and Sensory Feedback, *J. Biomed. Eng.* 10:189-195, Apr. 1988.
Assembly and Adjustment Instructions for 1P50-R, PROTEOR, Sep. 2004, pp. 1-21.
Au, S.K., et al., An EMG-Position Controlled System for an Active Ankle-Foot Prosthesis: An Initial Experimental Study, *Proceedings of the 2005 IEEE 9th International Conference on Rehabilitation Robotics*, Jun. 28-Jul. 1, 2005, Chicago, IL, pp. 375-379.
Bachmann, E., et al., Inertial and Magnetic Tracking of Limb Segment Orientation for Inserting Humans into Synthetic Environments, Naval Postgraduate School Dissertation, Dec. 2000.
Bar, A., et al., Adaptive Microcomputer Control of an Artificial Knee in Level Walking, *J. Biomechanical Eng.* 5:145-150, Apr. 1983.
Baten, C., et al., Inertial Sensing in Ambulatory Back Load Estimation, *18th Annual International Conference of the IEEE Engineering in Medicine and Biology Society*, Amsterdam, 1996, pp. 497-498.
Benedetti, M.G., Gait Analysis of Patients Affected by Post-Traumatic Ankle Arthrosis Treated with Osteochondral Allograft Transplantation, *SIAMOC 2006 Congress Abstracts/Gait & Posture*.
Blaya, J.A., et al., Adaptive Control of a Variable-Impedance Ankle-Foot Orthosis to Assist Drop-Foot Gait, *IEEE Transactions on Neural Systems and Rehabilitation Engineering* 12(1):24-31, Mar. 2004.
Blaya, J.A., Force-Controllable Ankle Foot Orthosis (AFO) to Assist Drop Foot Gait, Thesis, Massachusetts Institute of Technology, Jul. 8, 2003.
Bogert, A., et al., A Method for Inverse Dynamic Analysis Using Accelerometry, *J. Biomechanics* 29(7):949-954, 1996.

(56) References Cited

OTHER PUBLICATIONS

Bortz, J., A New Mathematical Formulation for Strapdown Inertial Navigation, *IEEE Transactions on Aerospace and Electronic Systems* AES-7(1), Jan. 1971.
Bouten, C.V., et al., A Triaxial Accelerometer and Portable Data Processing Unit for the Assessment of Daily Physical Activity, *IEEE Transactions on Biomedical Engineering* 44(3):136-147, Mar. 1997.
Bouten, C.V., et al., Assessment of Energy Expenditure for Physical Activity Using a Triaxial Accelerometer, *Medicine and Science in Sports and Exercise* 26(12)151-1523, Aug. 1994.
Crago, P.E., et al., New Control Strategies for Neuroprosthetic Systems, *Journal of Rehabilitation Research and Development* 33(2), Apr. 1996, 158-172.
Dai, R., et al. Application of Tilt Sensors in Functional Electrical Stimulation, *IEEE Transactions on Rehabilitation Engineering* 4(2):63-71, Jun. 1996.
Ferris, D.P., et al., An Ankle-Foot Orthosis Powered by Artificial Pneumatic Muscles, *Journal of Applied Biomechanics* 21:189-197, 2005.
Fisekovic, N., et al., New Controller for Functional Electrical Stimulation Systems, *Mediccal Engineering & Physics* 23:391-399, 2000.
Fite, K., et al., Design and Control of an Electrically Powered Knee Prosthesis, *Proceedings of the 2007 IEEE 10th International Conference on Rehabilitation Robotics*, Jun. 12-15, 2007, The Netherlands, pp. 902-905.
Foerster, F., et al., Detection of Posture and Motion by Accelerometry: A Validation Study in Ambulatory Monitoring, *Computers in Human Behavior* 15:571-583, 1999.
Foxlin, E., et al., Miniature 6-DOF Inertial System for Tracking HMDs, *SPIE* 3362, *Helmet and Head-Mounted Displays III, AeroSense 98*, Orlando, FL, Apr. 13-14, 1998.
Frank, K., et al., Reliable Real-Time Recognition of Motion Related Human Activities Using MEMS Inertial Sensors, no date.
Fujita, K., et al., Joint Angle Control with Command Filter for Human Ankle Movement Using Functional Electrical Stimulation, *Proceedings of the 9th Annual Conference of the IEEE Engineering in Medicine and Biology Society*, Boston, MA, Nov. 13-16, 1987.
Godha, S., et al., Integrated GPS/INS System for Pedestrian Navigation in a Signal Degraded Environment, *ION GNSS 2006*, Fort Worth, TX, Sep. 26-29, 2006, p. 1-14.
Graps, A., An Introduction to Wavelets, *IEEE Computational Science & Engineering*, pp. 50-61, Summer 1995.
Hanafusa, H., and H. Asada, A Robot Hand with Elastic Fingers and Its Application to Assembly Process, Robot Motion, Brady, et al., MIT Press, Cambridge, MA, 1982, pp. 337-359.
Hashimoto, M., and Y. Imamura, An Instrumented Compliant Wrist Using a Parallel Mechanism, *Japan/USA Symposium on Flexible Automation* 1:741-744, ASME, 1992.
Hayes, W.C., et al., Leg Motion Analysis During Gait by Multiaxial Accelerometry: Theoretical Foundations and Preliminary Validations, *Journal of Biomechanical Engineering* 105:283-289, Aug. 1983.
Heyn, A., et al., The Kinematics of the Swing Phase Obtained From Accelerometer and Gyroscope Measurements, *18th Annual International Conference of the IEEE Engineering in Medicine and Biology Society*, Amsterdam, 1996, pp. 463-464.
Howard, R.D., Joint and Actuator Design for Enhanced Stability in Robotic Force Control, Ph.D. Thesis, Massachusetts Institute of Technology, Department of Aeronautics and Astronautics, 1990.
Jonic, S., et al., Three Machine Learning Techniques for Automatic Determination of Rules to Control Locomotion, *IEEE Transactions on Biomedical Engineering* 46(3):300-310, Mar. 1999.
Kidder, S.M., et al., A System for the Analysis of Foot and Ankle Kinematics During Gait. *IEEE Transactions on Rehabilitation Engineering* 4(1):25-32, Mar. 1996.
Kirkwood, C.A., et al., Automatic Detection of Gait Events: A Case Study Using Inductive Learning Techniques *J. Biomed. Eng.* 11:511-516, 1989.

Van Der Kooij, H., et al., A Multisensory Integration Model of Human Stance Control, *Biol. Cybern.* 80:299-308, 1999.
Kostov, A., et al., Machine Learning in Control of Functional Electrical Stimulation Systems for Locomotion, *IEEE Transactions on Biomedical Engineering* 42(6):543-551, Jun. 1995.
Lafortune, M.A., Three Dimensional Acceleration of the Tibia During Walking and Running, *J. Biomechanics* 24(10)877-886, 1991.
Lee, S., and K. Mase, Activity and Location Recognition Using Wearable Sensors, *Pervasive Computing*, IEEE, 2002, pp. 24-32.
Light, L.H., et al., Skeletal Transients on Heel Strike in Normal Walking with Different Footwear, *J. Biomechanics* 13:477-480, 1980.
Luinge, H.J., Inertial Sensing of Movement, Doctoral Thesis, Twente University Press, Enschede, The Netherlands, 2002, pp. 9-13.
Martens, W.L.J., Exploring Information Content and Some Application of Body Mounted Piezo-Accelerometers, PhyVision b.v., Gemert, The Netherlands, no date.
Mayagoitia, R.E., et al., Accelerometer and Rate Gyroscope Measurement of Kinematics: An Inexpensive Alternative to Optical Motion Analysis Systems, *Journal of Biomechanics* 35:537-542, 2002.
Moe-Nilssen, R., A New Method for Evaluating Motor Control in Gait Under Real-Life Environmental Conditions, Part 1: The Instrument, *Clinical Biomechanics* 13:320-327, 1998.
Moe-Nilssen, R., A New Method for Evaluating Motor Control in Gait Under Real-Life Environmental Conditions, Part 2: Gait Analysis, *Clinical Biomechanics* 13:328-335, 1998.
Morris, J.R.W., Accelerometry—A Technique for the Measurement of Human Body Movements, *J. Biomechanics* 6:729-736, 1973.
OSSUR Academy, 2004 Course Descriptions, OSSUR North America, 16 pages.
Otto Bock, Quality for Life, Software C-Soft, Menu-driven Setting of the C-Leg, 2004, 1 page.
Otto Bock, C-Leg System, available at http://web.archive.org/web/20040215152410/http:/www.ottobockus.com/products/lower_limb_prosthetics/c-leg.asp [accessed Mar. 8, 2013].
Otto, J., Prosthetic Knees: What's Currently New and Impressive? The O&P Edge, http://www.oandp.com/edge/issues/articles/2003-10_03.asp, Oct. 2003, 4 pages.
Petrofsky, J.S., et al., Feedback Control System for Walking in Man, *Comput. Biol. Med.* 14(2):135-149, 1984.
Pfeffer, L.E., and R.H. Cannon, Jr., Experiments with a Dual-Armed, Cooperative, Flexible-Drivetrain Robot System, Proceedings of the 1993 IEEE International Conference on Robotics & Automation 3:601-608, May 5, 1993.
Popovic, D., et al., Control Aspects of Active Above-Knee Prosthesis, *International Journal of Man—Machine Studies* 35(6)751-767, Dec. 1991.
Raggi, M., et al. Wearable Sensors for the Real-Time Assessment of Gait Temporal Symmetry in Above-Knee Amputees: The 'SEAG' Protocol, *Abstracts of the 2007 SIAMOC Congress/Gait & Posture*, pp. 26-27.
Raggi, M., et al., Gait Analysis Through Inertial Sensors in Transfemoral Amputees: Step and Stride Regularity, *SIAMOC 2006 Congress Abstracts/Gait & Posture*, pp. S17-S18.
Rietman, J.S., et al., Gait Analysis in Prosthetics: Opinions, Ideas, and Conclusions, *Prosthetics and Orthotics International* 26:50-57, 2002.
Robinson, D.W., et al., Series Elastic Actuator Development for a Biomimetic Walking Robot, MIT Leg Laboratory, 1999.
Robinson, D.W., Design and Analysis of Series Elasticity in Closed-Loop Actuator Force Control, MIT Department of Mechanical Engineering, Jun. 1996.
Sekine, M., et al., Classification of Waist-Acceleration Signals in a Continuous Walking Record, *Medical Engineering & Physics* 22:285-291, 2000.
Sin, S.W., et al., Significance of Non-Level Walking on Transtibial Prosthesis Fitting with Particular Reference to the Effects of Anterior-Posterior Alignment, *Journal of Rehabilitation Research and Development* 38(1)1-6, Jan./Feb. 2001.

(56) References Cited

OTHER PUBLICATIONS

Smidt, G.L., et al., An Automated Accelerometry System for Gait Analysis, *J. Biomechanics* 10:367-375, 1977.

Sugano, S., et al., Force Control of the Robot Finger Joint equipped with Mechanical Compliance Adjuster, *Proceedings of the 1992 IEEE/RSJ International Conference on Intelligent Robots and Systems*, Raleigh, NC, Jul. 7-10, 1992, pp. 2005-2013.

Sup, F., and M. Goldfarb, Design and Control of a Powered Knee and Ankle Prosthesis, *2007 IEEE International Conference on Robotics and Automation*, Rome, Italy, Apr. 10-14, 2007, pp. 4134-4139.

Sup, F., et al., Design and Control of a Powered Transfemoral Prosthesis, *The International Journal of Robotics Research* 27:263-273, Feb. 2008.

Sup, F., et al., Design and Control of an Active Electrical Knee and Ankle Prosthesis, *Proceedings of the 2nd Biennial IEEE/RASEMBS International Conference on Biomedical Robotics and Biomechatronics*, Scottsdale, AZ, Oct. 19-22, 2008, pp. 523-528.

Sup, F., et al., Design of a Pneumatically Actuated Transfemoral Prosthesis, *Proceedings of IMECE2006: 2006 ASME International Mechanical Engineering Congress and Exposition*, Chicago, IL, Nov. 5-10, 2006.

Tong, K.Y., and M.H. Granat, Virtual Artificial Sensor Technique for Functional Electrical Stimulation, *Medical Engineering & Physics* 20:458-468, 1998.

Tong, K.Y., and M.H. Granat, A Practical Gait Analysis System Using Gyroscopes, Medical Engineering & Physics 21(2):87-94, Mar. 1999.

Varol, H.A., et al., Decomposition-Based Control for a Powered Knee and Ankle Transfemoral Prosthesis, *Proceedings of the 2007 IEEE 10th International Conference on Rehabilitation Robotics*, Jun. 12-15, 2007, Noordwijk, The Netherlands, pp. 783-789.

Varol, H.A., et al., Real-time Intent Recognition for a Powered Knee and Ankle Transfemoral Prosthesis, *Proceedings of the 2007 IEEE 10th International Conference on Rehabilitation Robotics*, Jun. 12-15, 2007, Noordwijk The Netherlands, pp. 16-23.

Varol, H.A., Real-Time Gait Mode Intent Recognition of a Powered Knee and Ankle Prosthesis for Standing and Walking, *Proceedings of the 2nd Biennial IEEE/RAS-EMBS International Conference on Biomedical Robotics and Biomechatronics*, Scottsdale, AZ, Oct. 19-22, 2008, pp. 66-72.

Veltink, P.H., et al., Detection of Static and Dynamic Activities Using Uniaxial Accelerometers, *IEEE Transactions on Rehabilitation Engineering* 4(4):375-385, 1996.

Willemsen, A.Th.M., et al., Real-Time Gait Assessment Utilizing a New Way of Accelerometry. *J. Biomechanics* 23(8):859-863, 1990.

Willemsen, A.Th.M., et al., Automatic Stance-Swing Phase Detection from Accelerometer Data for Peroneal Nerve Stimulation, *IEEE Transactions on Biomedical Engineering* 37(12):1201-1208, Dec. 1990.

Williamson, M.M., Series Elastic Actuators, *Massachusetts Institute of Technology Artificial Intelligence Laboratory, A.I. Technical Report No. 1524*, Jan. 1995, pp. 1-83.

Woodward, M.I., et al., Skeletal Accelerations Measured During Different Exercises, *Proceedings of the Institution of Mechinical Engineers, Part H: Journal of Engineering Medicine*, 207:79-85, 1993.

Wu, G., The Study of Kinematic Transients in Locomotion Using the Integrated Kinematic Sensor, *IEEE Transactions on Rehabilitation Engineering* 4(3):193-200, Sep. 1996.

Zamiska, N., Bionic Knee 'Learns' How to Walk, *The Wall Street Journal*, Jul. 6, 2004, p. D8.

"MT9 Inertial 3D Motion Tracker," Xsens Technologies B.V., available at http://www.xsens.com/download/MT9_brochure.pdf (at least as early as Oct. 2004), printed Jul. 20, 2006.

Advanced Materials & Processes, Sep. 2003, vol. 9, Issue 161, pp. 29-30, 3 pages.

Blaya, et al., "Adaptive Control of a Variable-Impedance Ankle-Foot Orthosis to Assist Drop-Foot Gait," IEEE Transactions on Neural Systems and Rehabilitation Engineering, vol. 12, No. 1; pp. 24-31, Mar. 2004.

Blaya, Force-Controllable Ankle Foot Orthosis (AFO) to Assist Drop Foot Gait, Feb. 2003 (believed to be catalogued on or after Jul. 8, 2003).

Blumentritt, Siegmar, Ph.D., et al., Design Principles, Biomedical Data and Clinical Experience With a Polycentric Knee Offering Controlled Stance Phase Knee Flexion: A Preliminary Report, Journal of Prothetics and Orthotics, 1997, vol. 1, Issue 9, pp. 18-24.

Carlson, What makes a Good MR Fluid?, 8th International Conference on Electrorheological (ER) Fluids and magnetorheological (MR) Suspensions, Nice 7 pages, Jul. 9-13, 2001.

Carlson et al., , "Smart Prosthetics Based on Magnetorheological Fluids", 8th Annual Symposium on Smart Structures and Materials, Mar. 2001.

Claiborne Jr., , "Making Inodes Behave,", Linux Journal, Publ. by SSC Inc., USA, Feb. 2001, No. 82, pp. 94-99.

Copes/Bionic Ankle, , The Most Significant Development in Ankle Prosthetics in Over a Half Century, 1985.

Elliott, Scott B., MR Microprocessor-Controlled Swing and Stance, Presentation to American Academy of Orthotists & Prosthetists, Feb. 4, 2004.

Gelat, Thierry et al., Adaptation of the gait initiation process for stepping on to a new level using a single step, Exp Brain Res (2000) 133:538-546, Jun. 21, 2000, pp. 9.

Grimes, An Active Multi-Mode Above-Knee Prosthesis Controller, Massachusetts Institute of Technology 1979, 158 pages, 1979.

Gronqvist, Raoul et al., Human-centered approaches in slipperiness measurement, Ergonomics, Oct. 20, 2001, vol. 44, Issue 13, pp. 1167-1199 (32 pages).

Hanson, James P. et al., Predicting slips and falls considering required and available friction, Ergonomics, 1999, vol. 42, Issue 12, pp. 1619-1633 (15 pages).

Herr et al. "User-adaptive control of a magnetorheological prosthetic knee", Industrial Robot: an International Journal, vol. 30, No. 1, (2003) pp. 42-55.

Herr, et al., Patient-Adaptive Prosthetic and Orthotic Leg Systems, 12th Nordic Baltic Conference on Biomedical Engineering and Medical Physics, Proceedings of the International Federation for Medical & Biological Engineering, 2002.

Herr, Presentation at "Experiencing the Frontiers of Biomedical Technology," (Mar. 10-11, 2003).

Hill, Stephen W. et al., Altered kinetic strategy for the control of swing limb elevation over obstacles in unilateral below-knee amputee gait, Journal of Biomechanics, 1999, vol. 32, pp. 545-549 (5 pages).

Jones, S. F. et al., The gait initiation process in unilateral lower-limb amputees when stepping up and stepping down to a new level, Clinical Biomechanics, 2005, vol. 20, pp. 405-413 (9 pages).

Kamiar Aminian et al., Estimation of Speed and Incline of Walking Using Neural Network, IEEE Transactions on Instrumentation and Measurement, vol. 44, No. 3, Jun. 1995, at 743.

Kirsner, Scott, A Step in the Right Direction Biomedical Horizons Expanding, Boston Globe, Mar. 17, 2003.

Kuster, M., et al., Kinematic and kinetic comparison of downhill and level walking, Clinical Biomechanics, 1995, vol. 10, Issue 2, pp. 79-84 (6 pages).

Lefebvre, "Permissions and Access Control Lists", UNIX Review's Performance Computing, Publ. by Miller Freeman, USA, Oct. 1998, vol. 16, No. 11, pp. 59-61.

Michel, V. et al., The strategies to regulate and to modulate the propulsive forces during gait initiation in lower limb amputees, Exp Brain Res, May 27, 2004, vol. 158, pp. 356-365 (10 pages).

Moseley, Anne M. et al., High- and low-ankle flexibility and motor task performance, Gait and Posture, 2003, vol. 18, pp. 73-80 (8 pages).

Nadeau, S. et al., Frontal and sagittal plane analyses of the stair climbing task in healthy adults aged over 40 years: what are the challenges compared to level walking?, Clinical Biomechanics, 2003, vol. 18, pp. 950-959 (10 pages).

(56) References Cited

OTHER PUBLICATIONS

Nakagawa, Intelligent Knee Mecahnism and the Possibility to Apply the Principle to the Other Joints, Engineering in Medicine and Biology Society, Proceedings of the 20th Annual International Conference of the IEEE, vol. 20, No. 5, Dec. 1998, at 2282.
Namespaces in XML,, World Wide Web Consortium Working Draft Sep. 16, 1998; Tim bray (Textuality); Dave Hollander (Hewlett-Packard Company); Andrew Layman (Microsoft).
Otto Bock , Orthopadische Industrie GMBH & Co., C-Leg Fitting Statistics (Abstract), Mar. 2000, 4 pages.
Otto Bock Orthopadische Industrie, C-LEG A new dimension in amputee mobility, Otto Bock Data Sheet, 1997.
Otto Bock Orthopadische Industrie, The Electronic C-Leg Compact Leg Prosthesis System: Instructions for Use, 2002.
Otto Bock Orthopadische Industrie, The Electronic C-Leg Knee Joint System: Instructions for Use, available at http://www.ottobockus.com/products/lower_limb_prosthetics/c-leg_instructions.pdf, 32 pages (printed Jul. 20, 2006).
Otto, "Prosthetic Knees: What's on the Way?", The O&P edge, http://www.oandp.com/edge/issues/articles/2003-10_02.asp, Oct. 2003, 5 pages.
Popovic et al. , Control Aspects of Active Above-Knee Prosthesis, International Journal of Man-Machine Studies, vol. 35, Isue 6, Dec. 1991, at 751.
Popovik, D., et al., Optimal Control for an Above-Knee Prosthesis With Two Degrees of Freedom, J. Biomechanics, 1995, vol. 1, Issue 28, pp. 89-98.
Powers, Christopher M. et al., Stair ambulation in persons with transtibial amputation: An analysis of the Seattle LightFootTM, Journal of Rehabilitation Research and Development, Jan. 1997, vol. 34, Issue 1, pp. 9-18 (10 pages).
Rao, Sreesha S. et al., Segment Velocities in Normal and Transtibial Amputees: Prosthetic Design Implications, IEEE Transactions on Rehabilitation Engineering, Jun. 1998, vol. 6, Issue 2, pp. 219-226 (8 pages).
Redfern, Mark S. et al., Biomechanics of descending ramps, Gait and Posture, 1997, vol. 6, pp. 119-125 (7 pages).
Riener, Robert et al., Stair ascent and descent at different inclinations, Gait and Posture, 2002, vol. 15, pp. 32-44 (13 pages).
State-Of-The Art Prosthetic Leg Incorporates Magneto-Rheological Technology, Medical Product Manufacturing News, Nov. 2000, pp. 42.
Suga, T., et al., "Newly designed computer controlled knee-ankle-foot orthosis (Intelligent Orthosis)", Prosthetics and Orthotics International, 1998, 22, 230-239.
Thakkar, Sneha, Energy Economy Gait Analysis of an Autoadaptive Prosthetic Knee, Master's Thesis submitted to the Dept. of Electrical Engineering and Computer Science, MIT, Dept. of Electrical Engineering and Computer Science, MIT, 2002, pp. 1-58.
Tomovic et al. , A Finite State Approach to the Syntesis of Bioengineering Control Systems, IEEE Transactions on Human Factors in Electronics, vol. HFE-7, No. 2, Jun. 1966.
Townsend M A et al., "Biomechanics and modeling of bipedal climbing and descending." Journal of Biomechanics 1976, vol. 9, No. 4, pp. 227-239, XP008078405.
U.S. Appl. No. 60/371,974 to Martin, filed Apr. 12, 2002 (from which U.S. Pat. No. 7,029,500, previously submitted, claims priority).
Van Der Loos, H.F.M., et al, ProVAR Assistive Robot System Architecture, Proceedings of the 1999 IEEE International Conference on Robotics & Automation; Detroit, Michigan, May 1999.
Veltink et al., The Feasibility of Posture and Movement Detection by Accelerometry, in 15th Annaul International Conference of the IEEE Engineering in Medicine and Biology Society, Oct. 28-31, 1993, San Diego, CA, 1230-1231.
Wilkenfeld, Ari Ph.D., et al., An Auto-Adaptive External Knee Prosthesis, Artificial Intelligence Laboratory, MIT, Cambridge, Massachusetts, Sep. 2000, pp. 3.
Wilkenfeld, Ari, Ph.D., Biologically inspired autoadaptive control of a knee prosthesis, Dissertation Abstract, MIT, Cambridge, Massachusetts, Sep. 2000, pp. 1.
Au, S. K., et al. Powered Ankle-Foot Prosthesis for the Improvement of Amputee Ambulation, Proceedings of the 29th Annual International Conference of the IEEE, Aug. 23-26, 2007.
Flowers, A Man-Interactive Simulator System for Above-Knee Prosthetics Studies, Aug. 1972.
Gard, Steven A., Ph.D., Use of Quantitative Gait Analysis for the Evaluation of Prosthetic Walking Performance, Journal of Prosthetics & Orthotics, vol. 18, Issue 6, pp. P93-P104, Jan. 2006.
McNealy, Lexyne L. and Steven A. Gard, Effect of Prosthetic Ankle Units on the Gait of Persons with Bilateral Trans-Femoral Amputations, Prosthetics and Orthotics International, 2008 32:111.
Murray, M. Pat, et al. Walking Patterns of Normal Men, The Journal of Bone and Joint Surgery, vol. 46-A, No. 2, Mar. 1964.
Perry, Jacquelin, MD, Gait Analysis: Normal and Pathological Function, 1992. (7 Parts).
Proteor, Assembly and Adjustment Instructions for IP50-R, pp. 1-21, Sep. 2004.
Sowell, T.T., A Preliminary Clinical Evaluation of the Mauch Hydraulic Foot-Ankle System, 5 Prosthetics and Orthotics International 87 (1981).
DIGINFO TV, "Powered Prosthetic Thigh and Leg", uploaded Nov. 7, 2008 http://www.youtube.com/watch?v=lqjtTzNEd54&feature=youtu.be%3E [Screenshots retrieved Oct. 23, 2014 in 9 pages].

\* cited by examiner

INSTRUMENTED PROSTHETIC FOOT

CROSS-REFERENCE TO RELATED APPLICATIONS

This application is a continuation of U.S. application Ser. No. 12/260,479, filed on Oct. 29, 2008, which is a continuation-in-part of U.S. application Ser. No. 10/715,989, filed on Nov. 18, 2003, now abandoned, the contents of which are incorporated herein by reference.

BACKGROUND OF THE INVENTION

Field of the Invention

The present invention relates to a prosthetic foot for use with a control system and/or a method for controlling an actuated leg prosthesis.

Description of the Related Art

As is well known to control engineers, the automation of complex mechanical systems is not something easy to achieve. Among such systems, conventional powered artificial limbs are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional prostheses do not have the capability to interact simultaneously with the human body and the external environment in order to have minimal appropriate functioning.

Accordingly, it is an object of the present application to obviate or mitigate some or all of the above disadvantages.

SUMMARY OF THE INVENTION

According to the present invention, there is provided an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

BRIEF DESCRIPTION OF THE DRAWINGS

Embodiments of the invention will be described by way of example only with reference to the accompanying drawings, in which.

DETAILED DESCRIPTION OF THE PREFERRED EMBODIMENT

The appended figures show a instrumented prosthetic foot (20) having sensors (22A, 22B) for use, in cooperation with possible additional sensors (24A, 24B, 26), with a control system (100) for controlling a prosthesis (14) having an actuating mechanism (16). It should be understood that the present invention is not limited to the illustrated implementation since various changes and modifications may be effected herein without departing from the scope of the appended claims.

Figure 1:
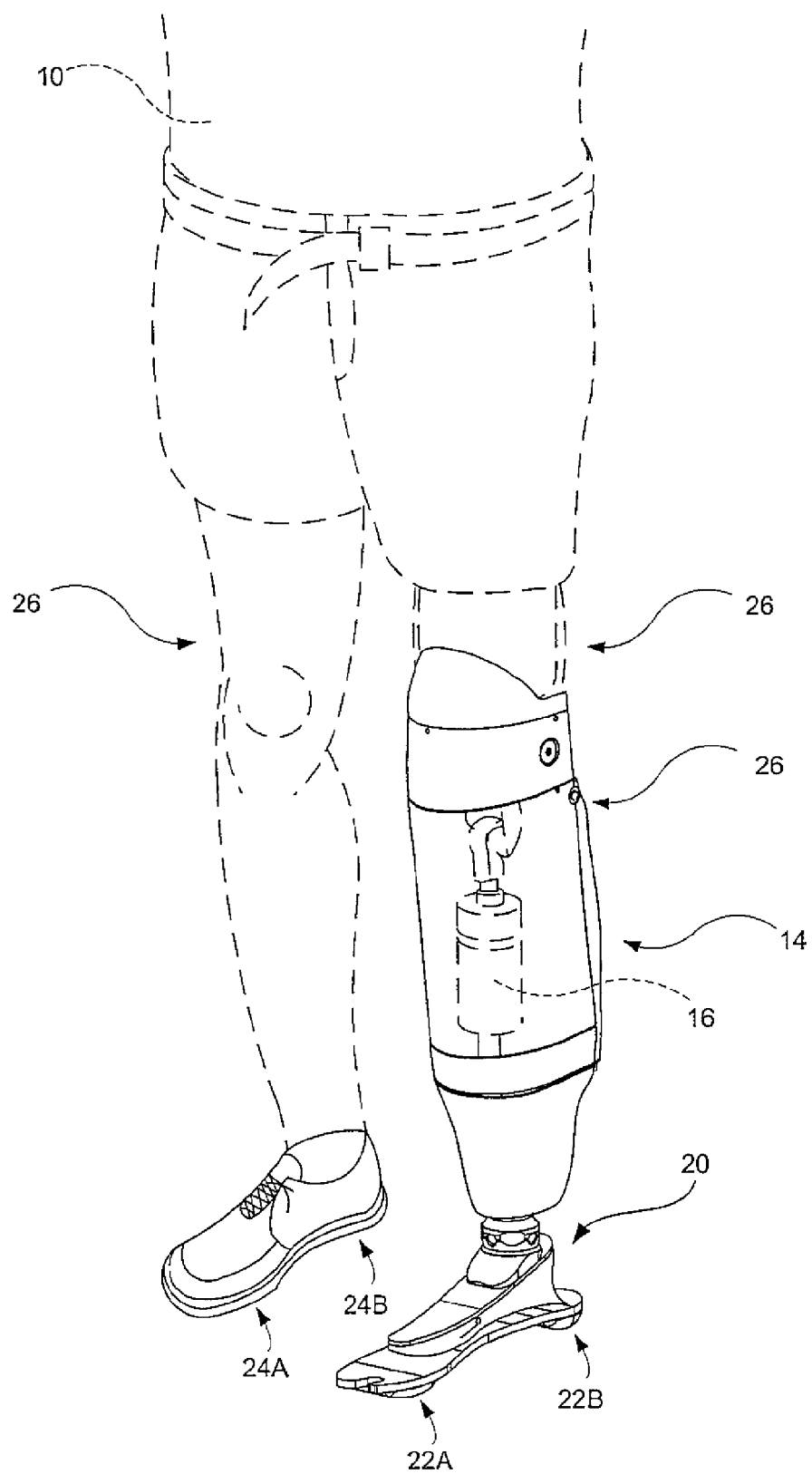
FIG. 1 shows the lower body of an individual provided with a prosthesis and an instrumented prosthetic foot on one side and having a healthy leg on the other side.

Referring therefore to FIG. 1 an individual (10) has a pair of legs (26) and (28), one of which, (26), is amputated above the knee. A prosthesis (14) is attached to the leg (26) and includes an actuating mechanism (16), which may be either passive or active. An instrumented prosthetic foot (20) is attached to the prosthesis (14) and includes sensors (22A, 22B). Additional sensors (24A, 24B) are located on the healthy foot and additional sensors (26) located on the individual (10) and/or the prosthesis (14). A passive actuating mechanism may be generally defined as an electromechanical component that only absorbs mechanical energy in order to modify dynamics of mechanical joints of the prosthesis, while an active actuating mechanism may be generally defined as an electro-mechanical component that absorbs and supplies mechanical energy in order to set dynamics of mechanical joints of the prosthesis.

An example of a passive actuating mechanism is described in U.S. patent application Ser. No. 09/767,367, filed Jan. 22, 2001, entitled "ELECTRONICALLY CONTROLLED PROSTHETIC KNEE". Examples of active actuating mechanisms are described in U.S. patent application Ser. No. 10/463,495 filed Jun. 17, 2003, entitled "ACTUATED PROSTHESIS FOR ABOVE-KNEE AMPUTEES", by Stéphane Bédard et al., the entire disclosure of which is hereby incorporated by reference herein.

Figure 2:
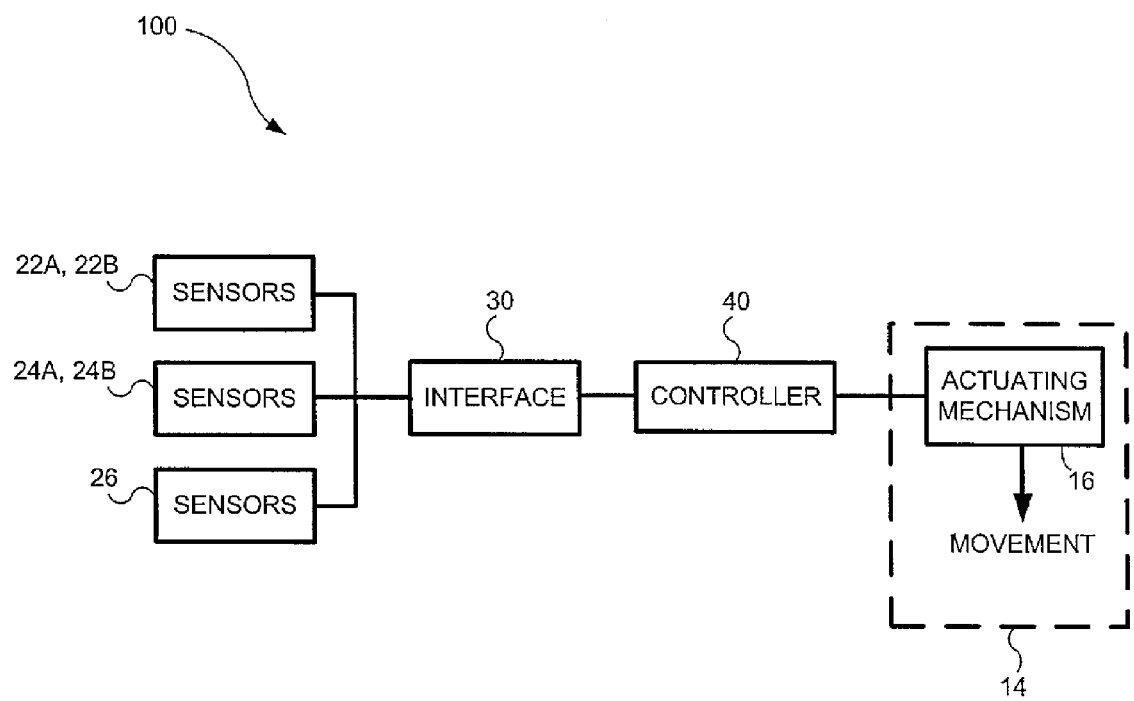
FIG. 2 is a block diagram showing a control system for a prosthesis having an actuating mechanism.

The prosthesis (14) is controlled, as shown schematically in FIG. 2, by a basic control system (100) comprising sensors (22A, 22B, 24A, 24B, 26), connected through an interface (30) to a controller (40). The controller (40) provides signals to an actuating mechanism (16) in the prosthesis (14), such as shown in FIG. 1. The purpose of the control system (100) is to provide the required signals for controlling the actuating mechanism (16). To do so, the control system (100) is interfaced with the amputee (10) using sensors (22A, 22B, 24A, 24B, 26) to ensure proper coordination between the amputee (10) and the movements of the prosthesis (14). The sensors (22A, 22B, 24A, 24B, 26) capture information, in real time, about the dynamics of the amputee's movement and provide that information to the controller (40) via the interface (30). The controller (40) then uses the information to determine the resistance to be applied to a joint, in the case of a passive actuating mechanism, or the joint trajectories and the required angular force or torque that must be applied by a joint, in the case of an active actuating mechanism, in order to provide coordinated movements.

The sensors (22A, 22B, 24A, 24B, 26) may include myoelectric sensors, neuro-sensors, kinematic sensors, kinetic sensors, strain gauges or plantar pressure sensors. Myoelectric sensors are electrodes used to measure the internal or the external myoelectrical activity of skeletal muscles. Neuro-sensors are electrodes used to measure the summation of one or more action potentials of peripheral nerves. Kinematic sensors are used to measure the position of articulated joints, the mobility speed or acceleration of lower extremities. Kinetic sensors are used to measure angular forces at articulated joints or reaction forces of lower extremities. Strain gages are used to measure the strain forces at a specific underfoot area. Plantar pressure sensors are used to measure the vertical plantar pressure of a specific underfoot area. Of course, additional types of sensors which provide various information about dynamics of human locomotion may be used. For a given application, the use of sensors (22A, 22B, 24A, 24B, 26) is not restricted to a specific type of sensor, multiple types of sensors in various combinations may be used.

As illustrated in FIG. 1, the sensors (22A, 22B) may comprise localized plantar pressure sensors located at spaced locations on the prosthetic foot (20) to measure the vertical plantar pressure of a specific underfoot area. Similarly, the plantar pressure sensors (24A, 24B) located on the side of the healthy foot may be provided at spaced locations in a custom-made insole, preferably in the form of a standard orthopedic insole, that is modified to embed the two sensors (24A, 24B) for the measurement of two localized plantar pressures. The sensors (22A, 22B, 24A, 24B) are operable to measure the weight transfer along the foot as the individual moves which may be combined with other sensors (26) such as kinematic sensors to measure the angular speed of body segments of the lower extremities and kinematic sensors to measure the angle of the prosthesis (14) knee joint.

Each sensor (22A, 22B, 24A, 24B) may comprise a thin Force-Sensing Resistor (FSR) polymer cell directly connected to the interface (30) of the control system (100) or indirectly using an intermediary system (not shown), for instance a wireless emitter. Of course, other types of communication link technologies may be used, such as, for example, optical. The FSR cell has a decreasing electrical resistance in response to an increasing force applied perpendicularly to the surface thereof. Each cell outputs a time variable electrical signal for which the intensity is proportional to the total vertical plantar pressure over its surface area. The size and position of the plantar pressure sensors (22A, 22B, 24A, 24B) may be defined in accordance with the stability and the richness (intensity) of the localized plantar pressure signals provided by certain underfoot areas during locomotion. For example, it was found by experimentation that the heel and the toe regions are two regions of the foot sole where the Plantar Pressure Maximum Variation (PPMV) may be considered as providing a signal that is both stable and rich in information.

Accordingly, the controller (40) may use the data signals from the four localized plantar pressure sensors (22A, 22B, 24A, 24B), as well as the information gathered from the data signals of the other sensors (26) such as kinematic sensors, in order to decompose the locomotion of the individual (10) into a finite number of states, and generate the appropriate control signals for controlling the actuating mechanism (16) according to the locomotion. Of course, the controller (40) is not limited to the use of the preceding data signals.

An example of a controller (40) and control system (100) using sensors comprising plantar pressure sensors as well as kinematic sensors is described in U.S. patent application Ser. No. 10/600,725 filed Jun. 20, 2003, entitled "CONTROL SYSTEM AND METHOD FOR CONTROLLING AN ACTUATED PROSTHESIS", by Stéphane Bédard, the entire disclosure of which is hereby incorporated by reference herein.

Figure 3:
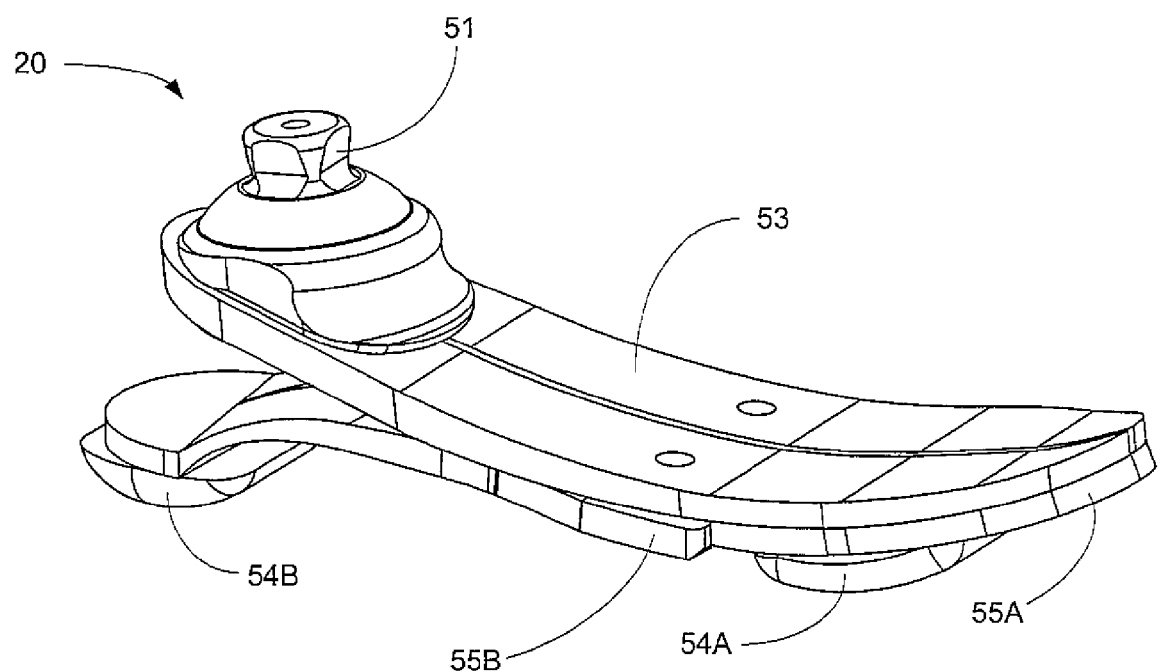
FIG. 3 is a perspective view, from the front and slightly above, of a instrumented prosthetic foot.
Figure 4:
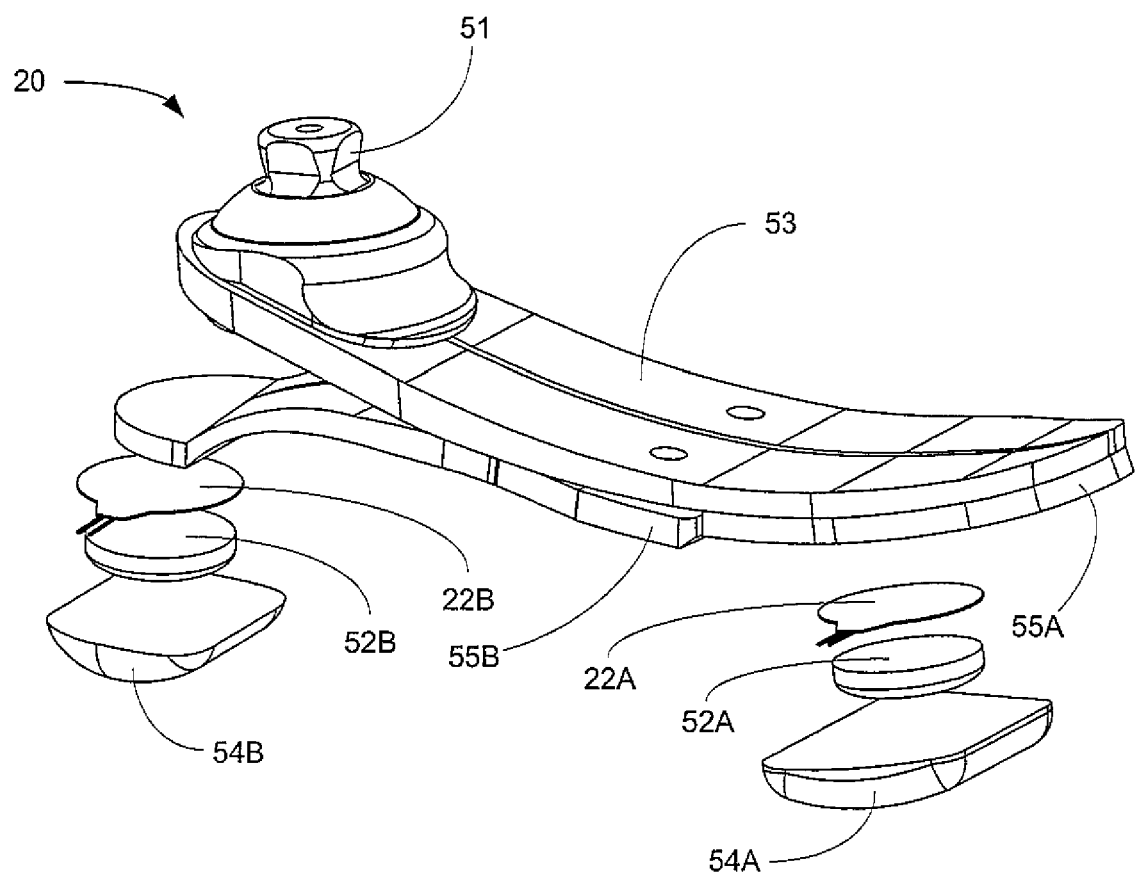
FIG. 4 is an exploded perspective view of the instrumented prosthetic foot of FIG. 3.

To facilitate the acquisition of the data in a repeatable and dependable manner, the sensors (22A, 22B) are incorporated in to the structure of the foot (20). An embodiment of the instrumented prosthetic foot (20) is shown in more detail in FIGS. 3 and 4. The instrumented prosthetic foot (20) includes a foot plate (53), forming an elongated body, with a connector (51) at one end, a toe plate (55A) and a heel plate (55B) that is cantilevered from the foot plate (53). Such an arrangement is provided by, for example, a Vari-Flex® prosthetic foot from Össur. Pressure sensors (22A, 22B) are located at longitudinally spaced locations on the underside of the foot plate (53) and heel plate (55) respectively. The sensors (22A, 22B) are covered by rigid plates (52A, 52B) and resilient pads (54A, 54B). The pressure sensors (22A, 22B) are located so as to be responsive to loads imposed on the instrumented prosthetic foot (20) at the regions corresponding to the toe area and the heel area respectively.

The rigid plates (52A, 52B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

The pads (54A, 54B) wrap up the rigid plates (52A, 52B) and the sensors (22A, 22B), forming a ground engaging member, in order to optimize the contact between the instrumented prosthetic foot (20) and the ground. The pads (54A, 54B) may be made of 40 A durometer polyurethane. Of course, other type of material may be used as well.

In operation, therefore, as the foot (20) traverses the ground, the force applied to the heel plate (55B) is measured by the sensor (22B) and a corresponding signal forwarded to the controller (40). The force applied to the toe plate (55A) is also measured by the sensor (22A) and the relative loading between the two locations is measured. As the foot (20) continues to traverse the ground, the force applied to the toe area increases and that at the heel decreases to provide a pair of signals from which the disposition of the leg may be determined and the appropriate control provided to the actuator (16).

Figure 5:
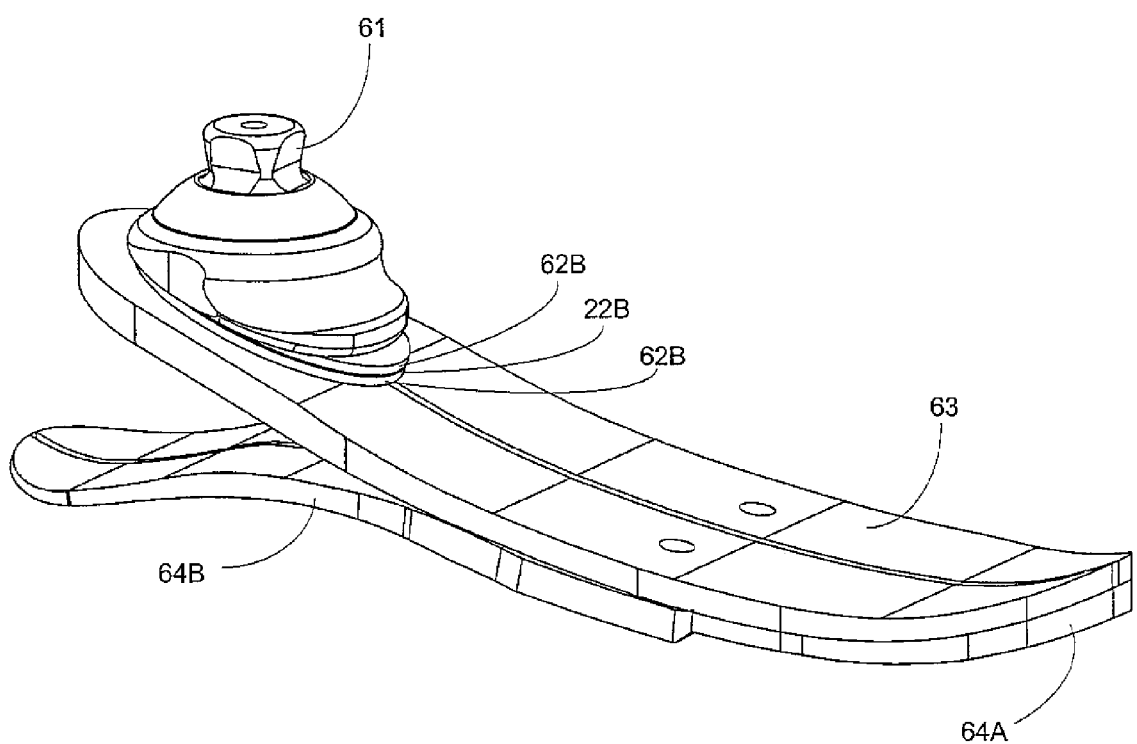
FIG. 5 is a perspective view, from the front and slightly above, of an alternative embodiment of the instrumented prosthetic foot of FIG. 3.
Figure 6:
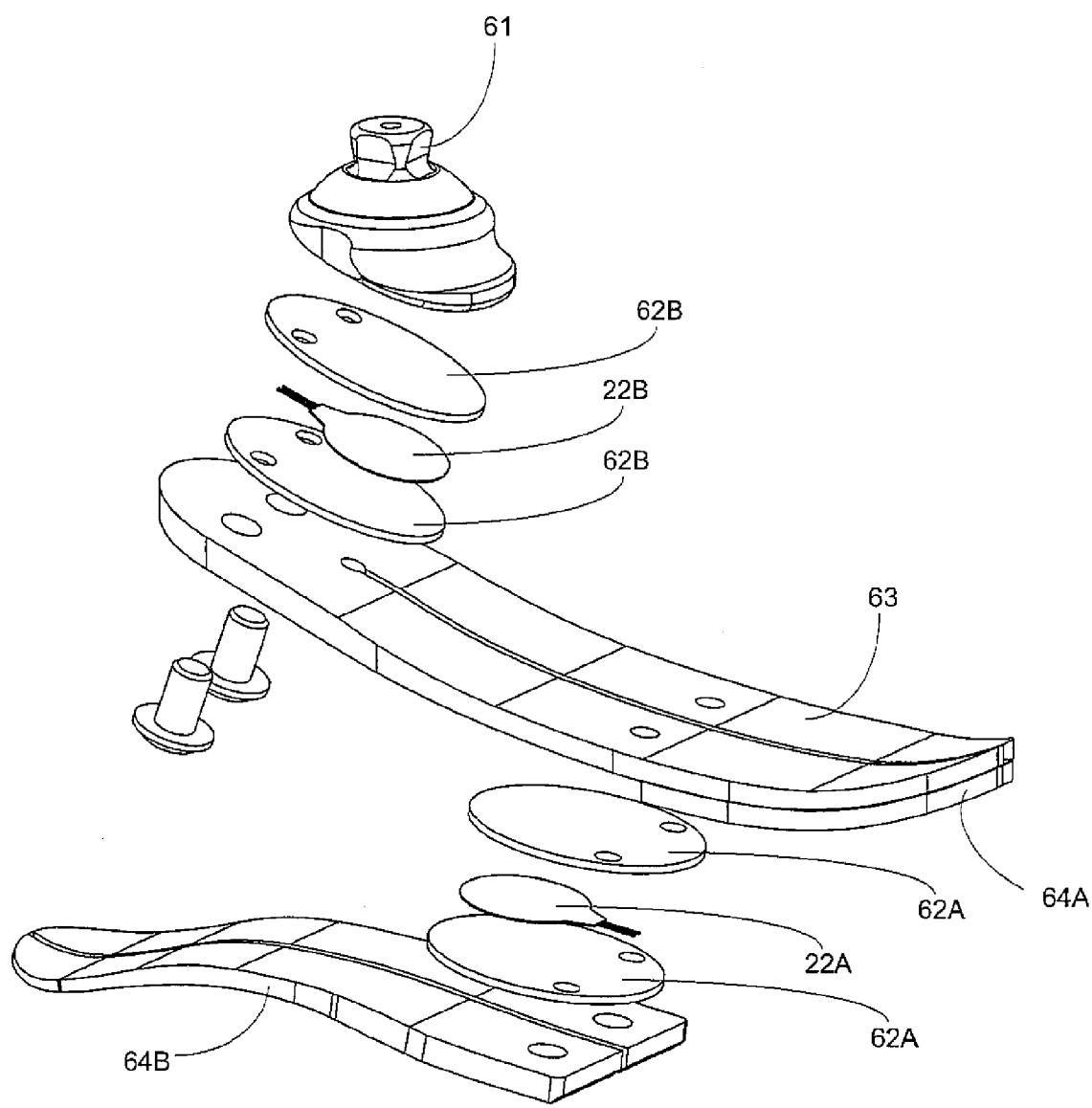
FIG. 6 is an exploded perspective view of the instrumented prosthetic foot of FIG. 5.

An alternative embodiment of the instrumented prosthetic foot (20) is shown in FIGS. 5 and 6. The instrumented prosthetic foot (20) includes connector (61), foot plate (63), toe plate (64A) and heel plate (64B), such as provided by, for example, a Vari-Flex® prosthetic foot from Össur. Pressure sensors (22A, 22B) are located between the foot plate (63) and rigid plates (62A, 62B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (62A), which in turn are positioned between the heel plate (64B) and the foot plate (63). Pressure sensor (22B) is sandwiched between a pair of rigid plates (62B), which in turn are positioned between the foot plate (63) and the connector (61).

As for the previous embodiment, rigid plates (62A, 62B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

Figure 7:
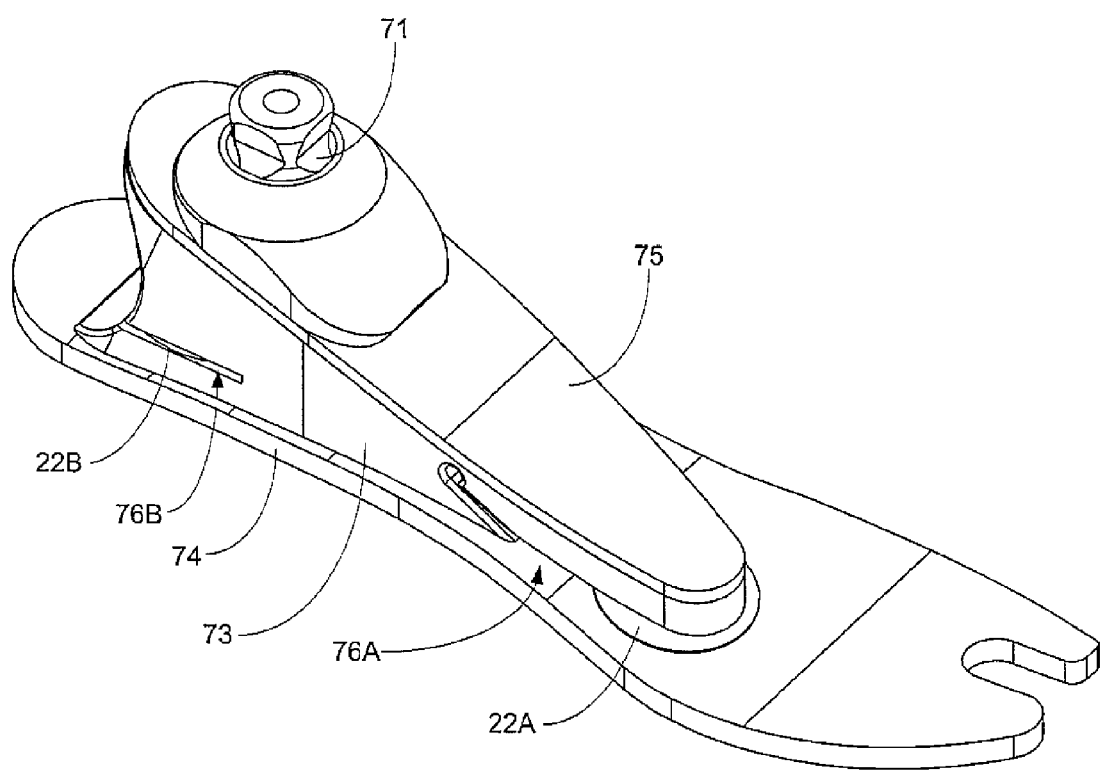
FIG. 7 is a perspective view, from the front and slightly above, of another alternative embodiment of the instrumented prosthetic foot of FIG. 3.
Figure 8:
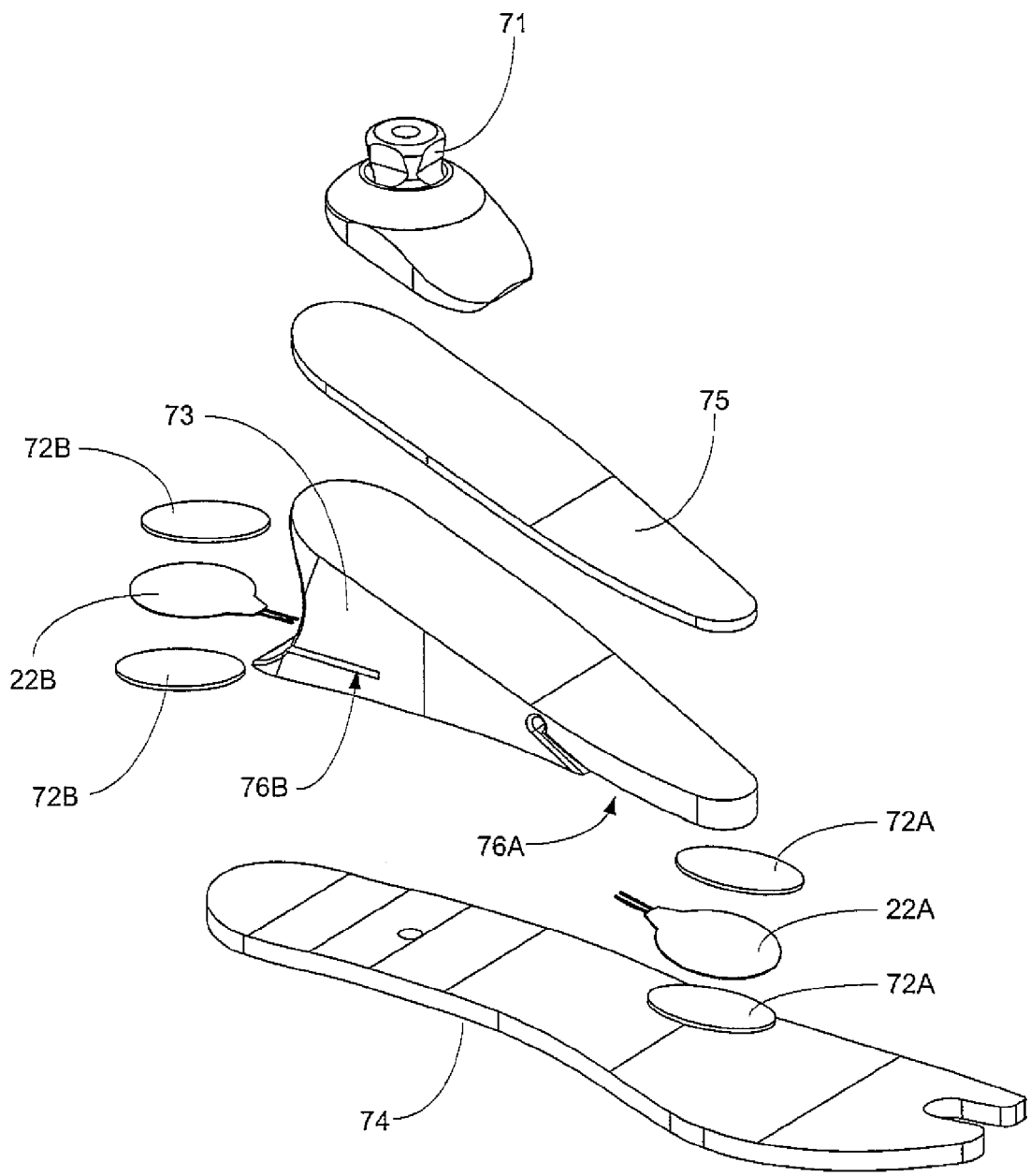
FIG. 8 is an exploded perspective view of the instrumented prosthetic foot of FIG. 7.

Another alternative embodiment of the instrumented prosthetic foot (20) is shown in FIGS. 7 and 8. The instrumented prosthetic foot (20) includes connector (71), top foot plate (75), foam cushion core (73) and bottom foot plate (74), such as provided by, for example, a LP Talux® prosthetic foot from Össur. Pressure sensors (22A, 22B) are sandwiched between pairs of rigid plates (72A, 72B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (72A), which in turn are positioned within gap (76A), which is located between a bottom foot plate (74) and a foam cushion core (73). Pressure sensor (22B) is sandwiched between a pair of rigid plates (72B), which in turn are positioned within gap (76B), which is located within the foam cushion core (73).

Again, as for the previous embodiments, rigid plates (72A, 72B) covering the sensors (22A, 22B), although not essential, help to optimize the pressure distribution on the entire surface of the sensors (22A, 22B) as well as preventing any shearing and may be made of 85 A durometer polyurethane. Of course, other type of material may be used as well.

Figure 9:
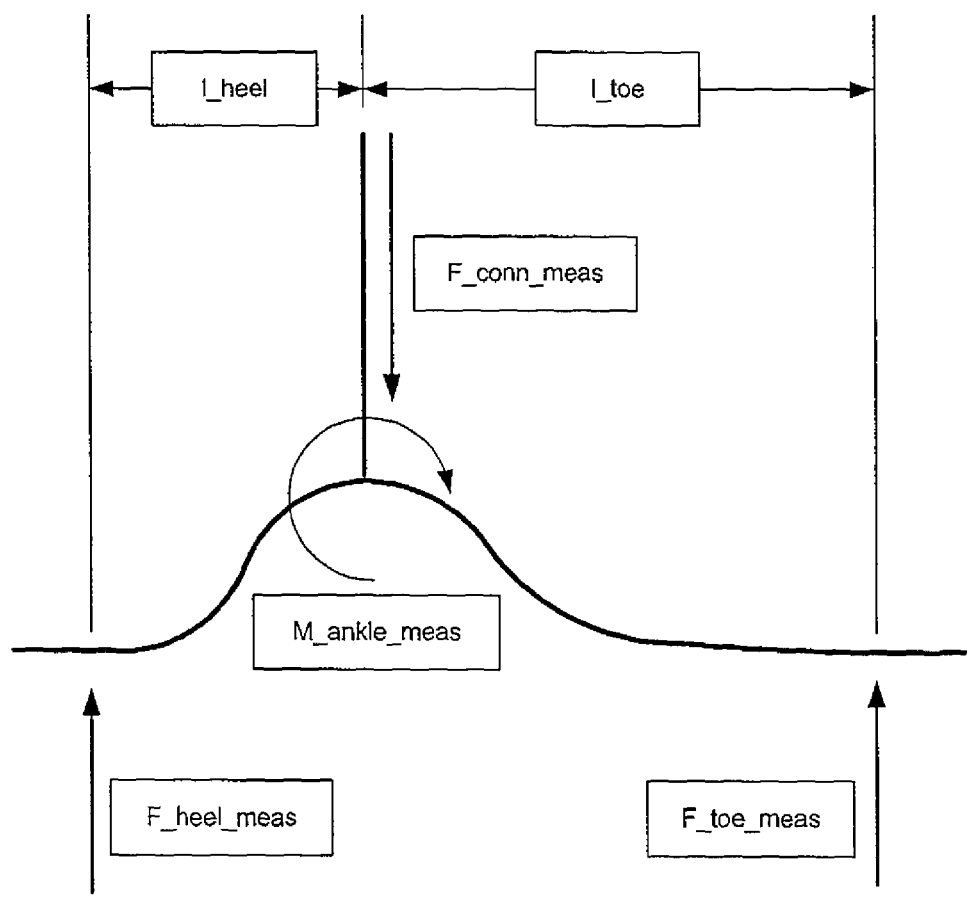
FIG. 9 is schematic view of forces exerted on a foot.

In the previous embodiments, the force (or pressure) at the toe and heel areas, F_toe and F_heel respectively, was obtained by positioning pressure sensors (22A, 22B) directly at those areas. More specifically, referring to FIG. 9, F_toe and F_heel were obtained as follows:

$$F\_toe = F\_toe\_meas \quad \text{Equation 1}$$

$$F\_heel = F\_heel\_meas \quad \text{Equation 2}$$

In other possible embodiments of the instrumented prosthetic foot (20), sensors (22A, 22B) may not be restricted to being positioned directly at the toe and heel areas, the equivalent information may be obtained by measuring the equivalent torque at the ankle and the axial force at the connector of the instrumented prosthetic foot (20). F_toe and F_heel may be defined in terms of the torque measured at the ankle, M_ankle_meas, and the force measured at the connector, F_conn_meas, using the following equations:

$$F\_toe = \frac{M\_ankle\_meas + (F\_conn\_meas \cdot l\_heel)}{(l\_heel + l\_toe)} \quad \text{Equation 3}$$

$$F\_heel = \frac{M\_ankle\_meas + (F\_conn\_meas \cdot l\_toe)}{(l\_heel + l\_toe)} \quad \text{Equation 4}$$

where l_heel is the distance between the center of the connector and the center of the heel area;

l_toe is the distance between the center of the connector and the center of the toe area.

Figure 10:
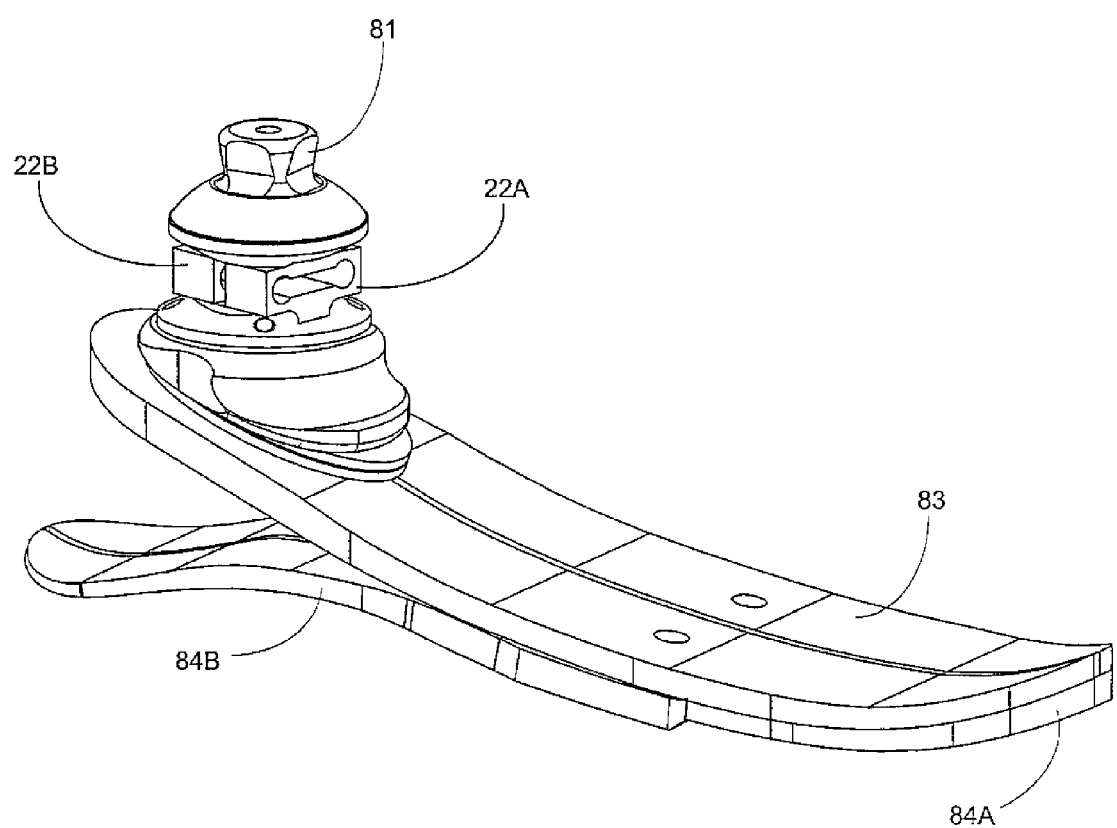
FIG. 10 is a perspective view, from the front and slightly above, of a further still alternative embodiment of the instrumented prosthetic foot of FIG. 3
Figure 11:
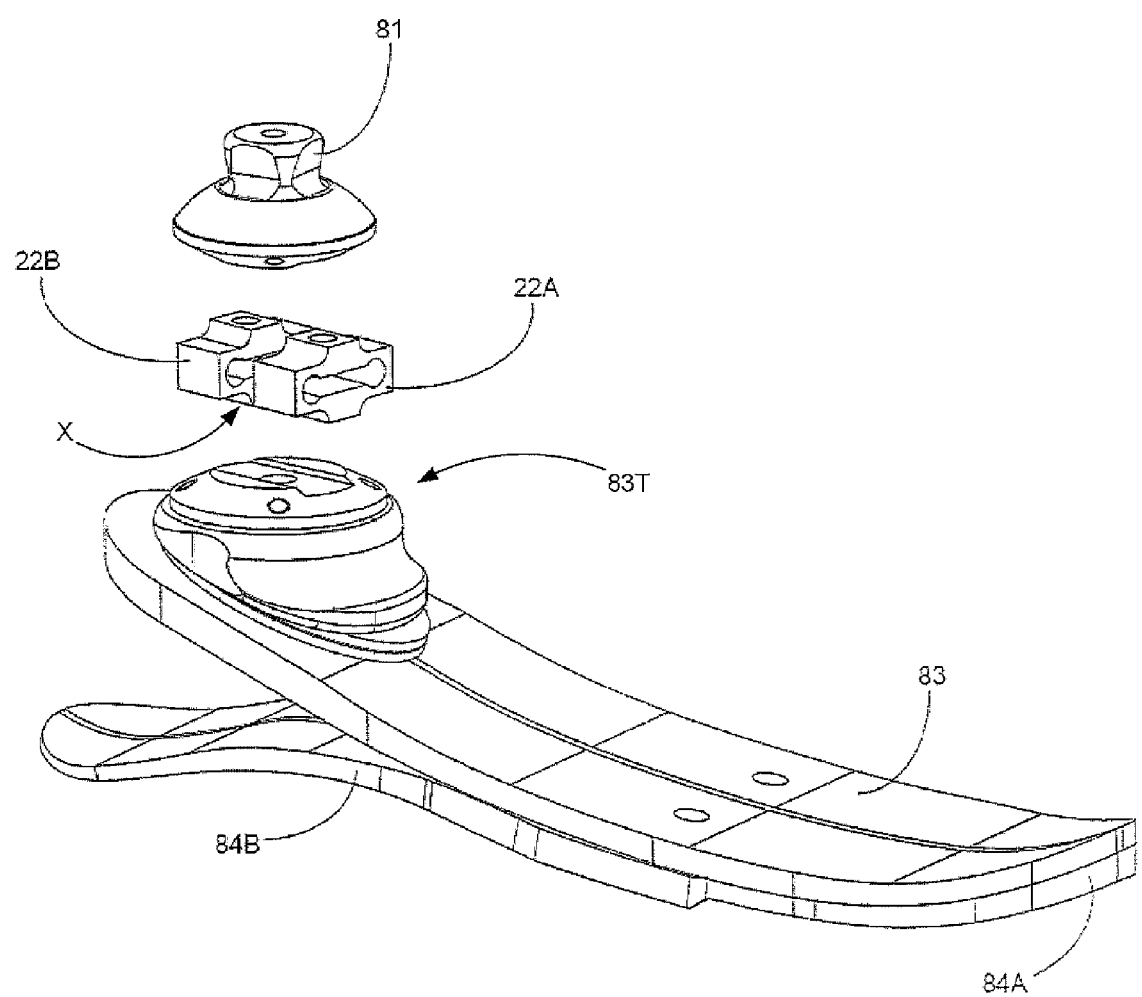
FIG. 11 is an exploded perspective view of the instrumented prosthetic foot of FIG. 10.

Following the previous discussion about the locations of sensors (22A, 22B), a further alternative embodiment of the instrumented prosthetic foot (20) is shown in FIGS. 10 and 11. The instrumented prosthetic foot (20) includes connector (81), an elongated body or foot plate (83), toe plate (84A) and heel plate (84B), such as provided by, for example, a Vari-Flex® prosthetic foot from Össur, and load cells (22A, 22B). Load cells (22A, 22B) are located below connector (81), load cell (22A) being slightly biased towards the toe area of the foot and load cell (22B) being slightly biased towards the heel area. The pair of load cells (22A, 22B) are positioned side by side and interposed between the connector (81) and the top part (83T) of the elongated body (83) and as such serve to both connect the foregoing together and to measure the load on the connector (81). The side by side load cells (22A, 22B) are in close proximity to one another and free of any load bearing element therebetween (area X in FIG. 11). In this way, the load cells (22A, 22B) support essentially the full load on the connector (81). As is known in the art, load cells are deformable (i.e. flexible, compressible and resilient). Therefore, the load cells (22A, 22B) are so deformed by the above-mentioned full load as to provide a multidirectional movement of the connector (81) relative to the elongated body (83). The foregoing is due to the fact that there is no other load bearing element between the load cells (22A, 22B), as is shown in area X, and the deformable nature of the load cells (22A, 22B) which allow the connector (81) to move in multiple directions relative to the elongated body (83). Thus, by not including any other load bearing element between the side by side proximate load cells 22A, 22B), these load cells 22A, 22B) can measure the load on the connector (81) during movement thereof in any direction including in the sagittal plane, in the coronal plane and/or in any plane between the both representing complex directions included into the corano-sagittal plane. Since the sensors (22A, 22B) are not located directly at the toe and heel areas, Equation 3 and Equation 4 may be used, for example by controller (40), to compute the equivalent pressures at the toe and heel areas by defining the equivalent torque at the ankle and the axial force at connector (81) as follows:

$$F\_conn\_meas = F\_22B + F\_22A \quad \text{Equation 5}$$

$$M\_ankle\_meas = F\_22B \cdot l\_22B - F\_22A \cdot l\_22A \quad \text{Equation 6}$$

where

F-22B is the force measured at sensor 22B;

F-22A is the force measured at sensor 22A;

l-22B is the distance between the center of the connector (81) and the center of sensor 22B;

l-22A is the distance between the center of the connector (81) and the center of sensor 22A.

Figure 12:
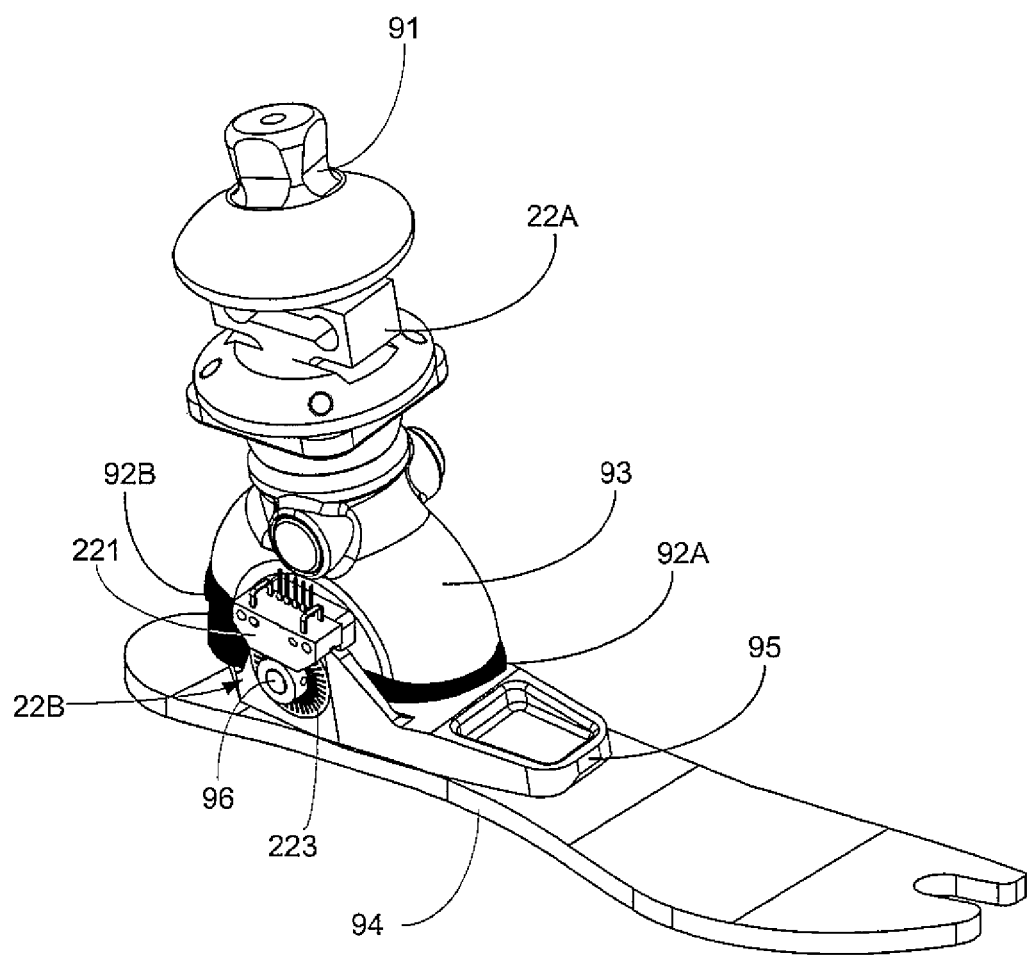
FIG. 12 is a perspective view, from the front and slightly above, of a yet further still alternative embodiment of the instrumented prosthetic foot of FIG. 3.
Figure 13:
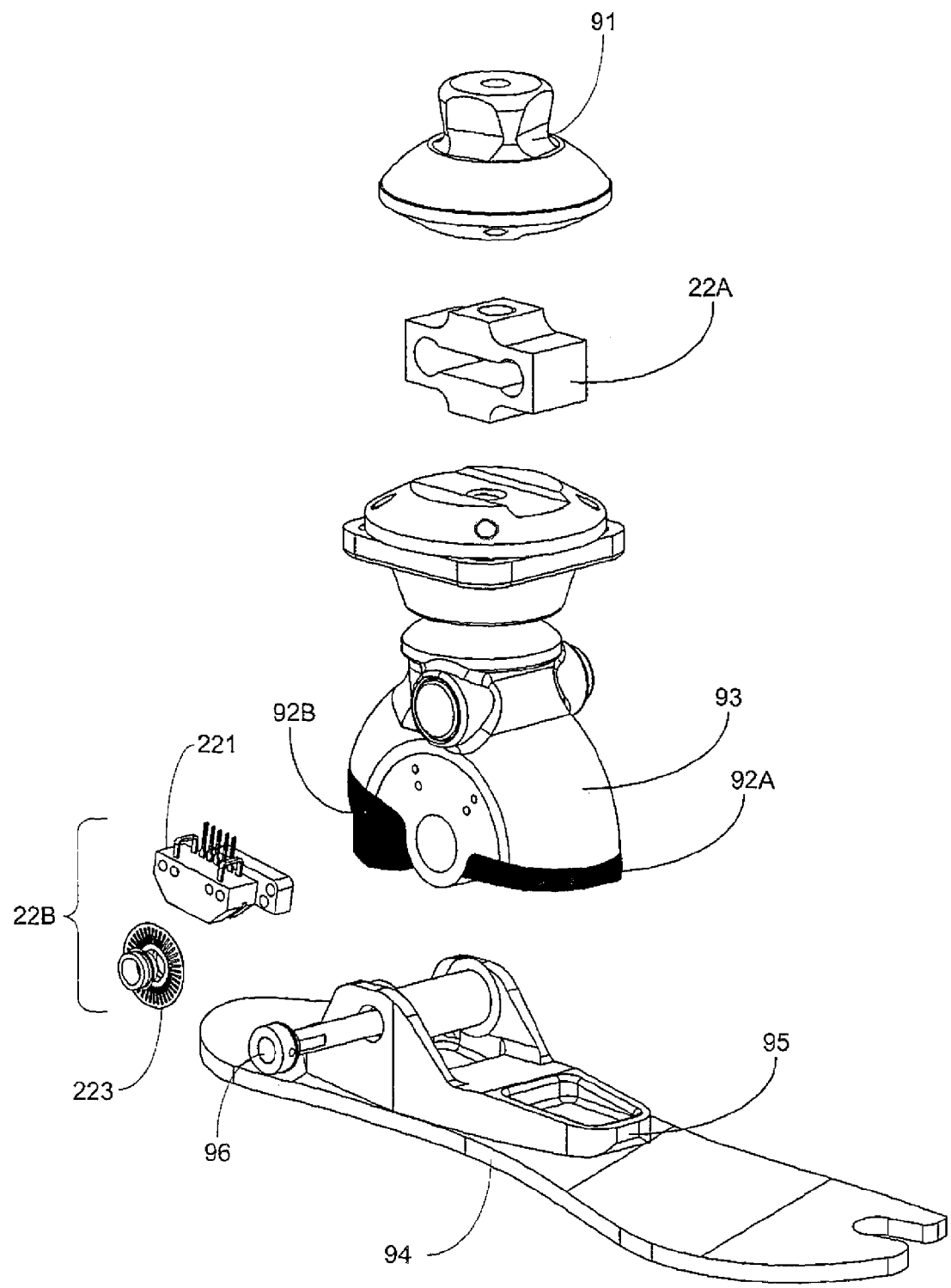
FIG. 13 is an exploded perspective view of the instrumented prosthetic foot of FIG. 12.

In the previous embodiments of the instrumented prosthetic foot (20), the force (or pressure) at the toe and heel areas, F_toe and F_heel respectively, was obtained either by positioning pressure sensors (22A, 22B) directly at those areas or by positioning pressure sensors or load cells (22A, 22B) in other areas and obtaining the equivalent information by computing the equivalent torque at the ankle and the axial force at the connector. Other types of sensors may also be used to obtain the equivalent torque at the ankle and the axial force at the connector. Such an example is illustrated by a further still embodiment of the instrumented prosthetic foot (20), which is shown in FIGS. 12 and 13. The instrumented prosthetic foot (20) includes connector (91), mounted on pivoting ankle (93). Bumpers (92A, 92B) are positioned between the pivoting ankle (93) and rocker plate (95) located on a foot plate (94). The pivoting ankle (93) is connected to the rocker plate (95) by a pivot pin (96). Such an arrangement is provided by, for example, an Elation® prosthetic foot from Össur. A load cell (22A) and an optical encoder (22B) are incorporated into the foot (20) to provide measurement of the distribution of forces along the foot (20). Load cell (22A) is positioned between connector (91) and pivoting ankle (93). Optical encoder (22B) comprises reader (221) and disk (223). Reader (221) is located on pivoting ankle (93) while disk (223) is located on rocker plate (95) and encircles pivot pin (96). Once again, Equation 3 and Equation 4 may be used, for example by controller (40), to compute the equivalent pressures at the toe and heel areas by defining the equivalent torque at the ankle and the axial force at connector (91) as follows:

$$F\_conn\_meas = F\_22A \qquad \text{Equation 7}$$

$$M\_ankle\_meas = R\_ankle\_meas \cdot R\_const \qquad \text{Equation 8}$$

where

F-22A is the force measured at sensor 22A;

R_ankle_meas is the rotation measurement of pivoting ankle (93) about pivot pin (96) as measured by optical encoder (22B);

R_const is a constant associated with the resistance of bumpers (92A, 92B) to compression, which constant varies depending in the material used.

Figure 14:
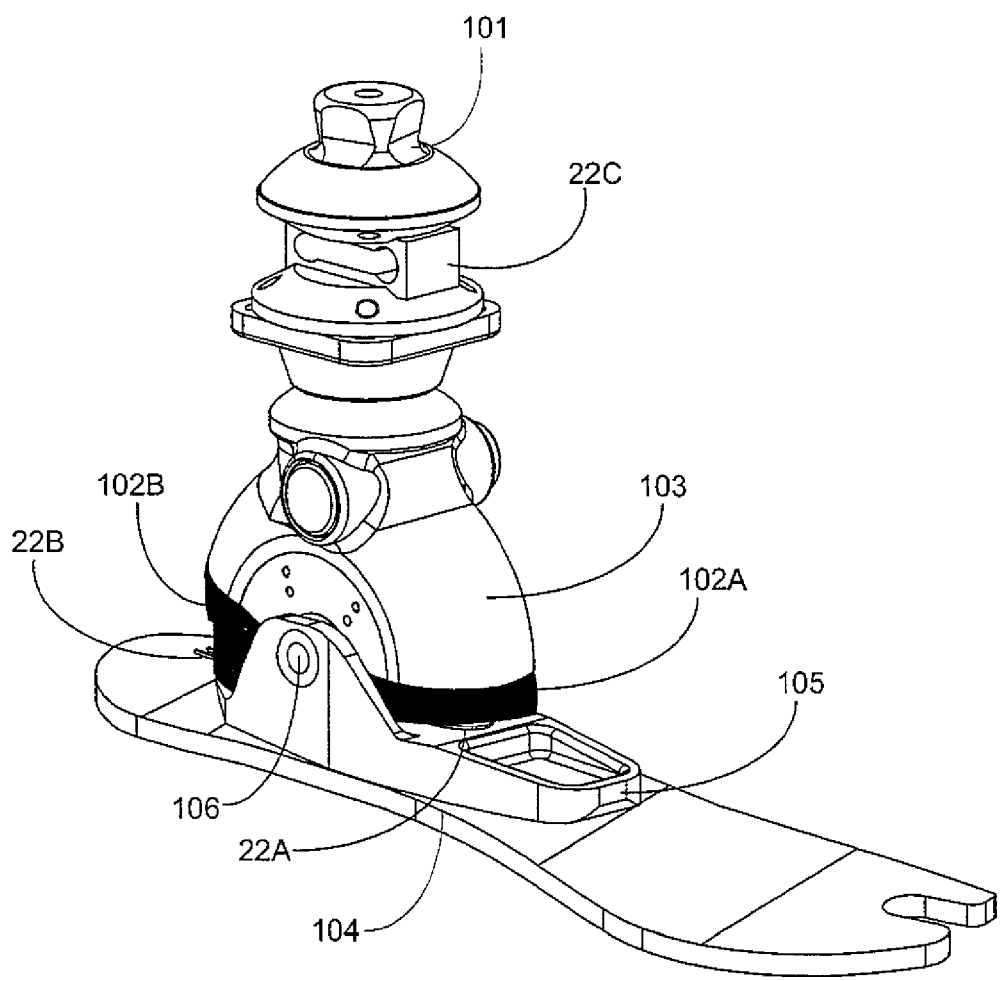
FIG. 14 is a perspective view, from the front and slightly above, of a further alternative embodiment of the instrumented prosthetic foot of FIG. 3.
Figure 15:
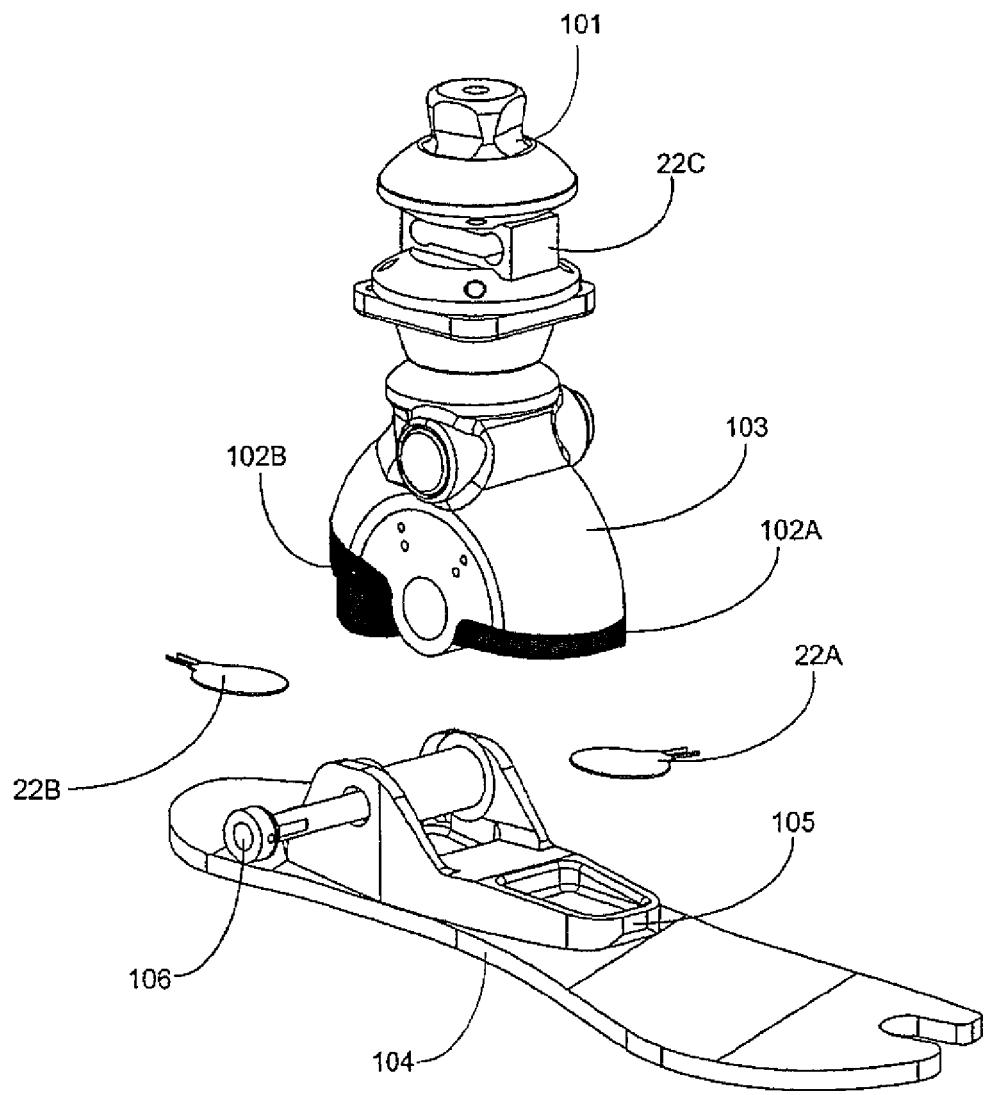
FIG. 15 is an exploded perspective view of the instrumented prosthetic foot of FIG. 14.

A yet further alternative embodiment of the instrumented prosthetic foot (20) is shown in FIGS. 14 and 15. The instrumented prosthetic foot (20) includes connector (101), mounted on pivoting ankle (103). Bumpers (102A, 102B) are positioned between the pivoting ankle (103) and rocker plate (105) located on a foot plate (104). The pivoting ankle (103) is connected to the rocker plate (105) by a pivot pin (106). Such an arrangement is provided by, for example, an Elation® prosthetic foot from Össur. Pressure sensors (22A, 22B) and load cell (22C) are incorporated into the foot (20) to provide measurement of the distribution of forces along the foot (20). Pressure sensor (22A) is positioned between rocker plate (85) and bumper (82A) while pressure sensor (22B) is positioned between rocker plate (85) and bumper (82B). A load cell (22C) is positioned between connector (91) and pivoting ankle (93).

In this embodiment, Equation 6 is used to compute the equivalent torque at the ankle, while the axial force at connector (101) is computed using the following equation:

$$F\_conn\_meas = F-22C \qquad \text{Equation 9}$$

Load cell (22C) is required to compute the axial force at connector (101) since when there is no torque at the ankle, i.e. the wearer of the prosthesis is standing still, the axial force is being exerted in its entirety onto pivot pin (96).

In all of the described embodiments, the sensors (22A, 22B) may be directly connected to interface (30) of control system (100) or indirectly using an intermediary system (not shown), for instance a wireless emitter. Of course, other types of communication link technologies may be used, such as, for example, optical.

Other types of non-articulated or articulated prosthetic foot may be used as well as long as the selected prosthetic foot provides approximately the same dynamical response as the ones mentioned here above. Nevertheless, an articulated foot offers the best performances. The instrumented prosthetic foot (20) may further have an exposed metal or composite structure or it may have a cosmetic covering that gives it the appearance of a human ankle and foot.

It should be noted that the present invention is not limited to its use with the mechanical configuration illustrated in FIG. 1 or the control system (100) illustrated in FIG. 2. It may be used with a leg prosthesis having more than one joint. For instance, it may be used with a prosthesis having an ankle joint, a metatarsophalangeal joint or a hip joint in addition to a knee joint. Moreover, instead of a conventional socket a osseo-integrated devices could also be used, ensuring a direct attachment between the mechanical component of the prosthesis and the amputee skeleton. Other kinds of prostheses may be used as well.

What is claimed is:

1. A prosthetic foot comprising:
   an elongated foot plate;
   a connector to operably connect the elongated foot plate to a user, the connector being connected in a manner that provides for multidirectional movement of the connector relative to the elongated foot plate;
   at least one solid sensor positioned between the connector and the elongated foot plate and positioned directly beneath the connector, the at least one solid sensor comprising a deformable material to provide for said multidirectional movement and configured to measure load on the prosthetic foot based on deformation of the deformable material; and
   a controller in communication with the at least one sensor and configured to communicate control signals to a device separate from the prosthetic foot based on data from the at least one sensor.

2. The prosthetic foot of claim 1, wherein the connector comprises a pyramid connector to removably connect the prosthetic foot to the user.

3. The prosthetic foot of claim 1, wherein the at least one solid sensor is free of other load-bearing elements.

4. A prosthetic foot comprising:
   an elongated foot plate;
   a connector to operably connect the elongated foot plate to a user, the connector being connected in a manner that provides for multidirectional movement of the connector relative to the elongated foot plate;
   at least one solid sensor positioned between the connector and the elongate foot plate and configured to measure load on the prosthetic foot; and
   a controller configured to communicate control signals to a device separate from the prosthetic foot at least partially based on an input from the at least one solid sensor.

5. The prosthetic foot of claim 4, wherein the at least one solid sensor is in contact with the connector and the elongate foot plate, the at least one solid sensor comprising a deformable material to provide for said multidirectional movement.

6. The prosthetic foot of claim 4, wherein the at least one sensor senses the load in any direction.

7. The prosthetic foot of claim 4, wherein the at least one sensor is in communication with the controller by a wired connection.

8. The prosthetic foot of claim 4, wherein the at least one sensor is in communication with the controller by a wireless connection.

9. The prosthetic foot of claim 4, wherein the at least one sensor comprises a pair of load sensors, wherein the pair of load sensors is free of other load-bearing elements.

* * * * *